(12) United States Patent
Lee et al.

(10) Patent No.: US 6,510,738 B1
(45) Date of Patent: Jan. 28, 2003

(54) DEVICE AND METHOD FOR MEASURING VIBRATION

(75) Inventors: Chih-Kung Lee; Chih-Ting Lin, both of Taipei; Wen-Hsin Hsiao, Taichung; Hsueh-Ching Shih, Taipei, all of (TW)

(73) Assignee: National Science Council, Taipei (TW)

( * ) Notice: Subject to any disclaimer, the term of this patent is extended or adjusted under 35 U.S.C. 154(b) by 179 days.

(21) Appl. No.: 09/635,991

(22) Filed: Aug. 9, 2000

(30) Foreign Application Priority Data

Aug. 9, 1999 (TW) .................................. 88113591 A

(51) Int. Cl.$^7$ ...................... H01L 41/047; G01P 15/09; G01H 11/08
(52) U.S. Cl. .................. 73/579; 73/662; 73/514.29; 310/312; 310/365; 310/366; 310/369
(58) Field of Search .................... 73/662, 579, 514.29; 310/312, 366, 317, 369, 365

(56) References Cited

U.S. PATENT DOCUMENTS

| | | | | |
|---|---|---|---|---|
| 3,638,146 A | * | 1/1972 | Takaku et al. ............... | 310/366 |
| 4,211,947 A | * | 7/1980 | Ikeno et al. ................ | 310/312 |
| 4,370,584 A | * | 1/1983 | Ikeno et al. ................ | 310/312 |
| 4,649,310 A | * | 3/1987 | Nakamura et al. .......... | 29/25.35 |
| 4,760,358 A | * | 7/1988 | Inoue ......................... | 310/366 |
| 4,868,447 A | | 9/1989 | Lee et al. .............. | 310/316.01 |
| 5,041,754 A | * | 8/1991 | Smythe ....................... | 310/317 |
| 5,521,772 A | | 5/1996 | Lee et al. ...................... | 360/69 |
| 5,824,903 A | * | 10/1998 | Nakamura et al. ........ | 73/514.29 |

OTHER PUBLICATIONS

Fukada, E., and Sakurai, T., "Piezoelectricity in Polarized Poly(vinylindene fluoride) Films," *Polymer Journal*, vol. 2, No. 5, pp. 656–662, 1971.
Kawai, H., "The Piezoelectricity of Poly(vinylidene Fluoride)," *Jpn. J. Appl. Phys.*, vol. 8, pp. 975–976, 1969.
Wada, Y. and Hayakawa, R., "Piezoelectricity and Pyroelectricity of Polymers," *Jpn. J. Appl. Phys.*, vol. 15, No. 11, pp. 2041–2057, Nov. 1976.
Furukawa T., Date, M. and Fukada, E., "Hysteresis Phenonmenon in Polyvinylidene Flouride Under High Electric Field," *J. Appl. Phys.*, vol. 51, pp. 1135–1141, 1980.
Cady W. G., "The Piezo–Electric Resonator," *POhys. Rev.*, vol. 17, p. 531, 1921.
Miller, D. W., Collins, S.A., and Peltzman, S.P., "Development of Spatially Convolving Sensors for Structural Control Applications," *Proceedings of the AIAA/ASME/ASCE/AHS Structures, Structural Dynamics and Materials Conference*, Long Beach, CA pp. 2283–2297, 1990.
Franks, L.E., *Signal Theory*, Prentice–Hall, Englewood Cliffs, N.J., pp. 136–137, 1969.
Fukada, E., "Piezoelectricity in Polymers and Biological Materials," *Ultrasonics*, vol. 6, No. 4, pp. 229–234,1968.
Murayama, N. Nakamura, K., Obara, H. and Segawa, M., "The Strong Piezoelectricity in Polyvinylidene Fluoride (PVDF)," *Ultrasonics*, vol. 14, pp. 15–23, 1976.
Meirovitch, L. and Baruh, H., "Control on Self–Adjoint Distrbuted–Parameter Systems," *J. Guid. and Contr.*, vol. 5, No. 1, pp. 60–66, 1982.
Meirovitch, L. and Baruh, H., "The Implementation of Modal Filters for Control of Structures," *J. Guid and Contr.*, vol. 8, No. 6, pp. 707–716, Nov. 1985.

* cited by examiner

*Primary Examiner*—Hezron Williams
*Assistant Examiner*—Rose M. Miller
(74) *Attorney, Agent, or Firm*—Knobbe, Martens, Olson & Bear, LLP

(57) ABSTRACT

The present invention discloses a vibration measuring device for measuring a vibration of an object. Such device includes a sensing body generating a dynamic information in response to the vibration, and a piezoelectric sensing layer disposed on the sensing body to construct a sensor and formed in a distributed mode to measure the dynamic information in a selected specific bandwidth. The present invention also discloses a vibration measuring method.

35 Claims, 13 Drawing Sheets

DEVICE AND METHOD FOR MEASURING VIBRATION

FIELD OF THE INVENTION

The present invention relates to device and method for measurement, and more particularly to device and method for measuring vibration.

BACKGROUND OF THE INVENTION

Conventionally, sensors include two primary categories such as the point sensor and the distributed sensor. For the former, it usually has bandwidth limitation as a result of its structural frequency response. The latter, such as the one disclosed in U.S. Pat. No. 4,868,447, includes the mode sensor and is closely related to the measured structural body.

Since the measurement of acceleration or acceleration rate is a very important information in vibration of the structure system, the accelerometer is directly put into measuring the acceleration at present. Accelerometers normally are of piezoelectric type or capacitance type. The former relates to an interaction between mechanical energy and electrical energy, which was found in 1880 by Curie brothers, i.e. Pierre Curie and Jacques Curie upon studying the relation between pyroelectric phenomenon and crystal symmetry. (Cady, 1964)

Curie brothers found that when the tourmaline is applied with stress, one can obtain the charge from the surface thereof. They subsequently found such phenomenon in a series of materials, e.g. zinc blende, calamine, boracite, sodium chlorate, quartz and Rochelle salt. The electrical polarization phenomenon produced with the deformation of such materials is called piezoelectricity.

Common piezoelectrical materials generally have three categories, i.e. natural crystal, piezoelectric ceramics and piezoelectric polymer. Since it is very difficult to make a distributed sensor through a natural crystal, e.g. quartz, only piezoelectric ceramics and piezoelectric polymer will be discussed here. Because piezoelectric ceramics, e.g. lead zirconate titanate (PZT) has higher coupling factor and dielectric constant, it is suitable for use in the driving device requiring a large driving force.

Current methods for measuring the acceleration rate are generally achieved by modifying the interface circuit of the accelerometer as disclosed in U.S. Pat. No. 5,521,772. The system response and the bandwidth of the conventional point sensor, no matter whether piezoelectric accelerometers or capacitance accelerometers are concerned, are limited by the frequency response of the sensor structure. In other words, the influence of the electronic circuit on the performance, the bandwidth, gain and phase angle of the conventional accelerometer are not only influenced by the interface electronic circuit but also primarily controlled by structural design of the sensor. General basic requirements of an excellent accelerometer are as follows: high electromechanical conversion efficiency, larger dynamic range, broader bandwidth response, higher stability, light weight, low transverse sensitivity and low environmental sensitivities in respect of factors including temperature, humidity and electromagnetic interference. It is not easy for the point sensor mentioned above, which is subjected to limitations of structural characteristics of its matching sensor, to meet with all design requirements at the same time.

To take the piezoelectric accelerometer as an example, after the piezoelectric material is applied with the accelerometer since 1960, the piezoelectric accelerometer has been extensively put into use in various fields. Generally speaking, apparent advantages of adopting the piezoelectric material as the sensing element of accelerometer include: light weight, small bulk, high reliability and self generation without external power supply necessary for the capacitance accelerometer. The bandwidth limitation of the accelerometer is primarily dominated by the sensor structure. Accelerometers using the piezoelectric material as the sensing element have the following featured designs:

1) Compression design: As shown in FIG. 1, the base 11, i.e. the sensor structure, supporting thereon the piezoelectric material 12, i.e. the sensing element, is connected to the external cover 13 to generate the acceleration signal through compressed deformation of the piezoelectric material;

2) Cantilever design: As shown in FIG. 2, the base 21 serves as the fixed end of the cantilever beam 22 formed by the piezoelectric material, whose free end is fixed to a mass 23 for increasing the acceleration response. The acceleration signal is measured through the strain generated by vibration of the cantilever beam 22;

3) Shear design: As shown in FIG. 3, it includes a base 31, a piezoelectric material 32 and an added mass 33. The signal is generated through the shear strain of the piezoelectric material;

4) Single ended compression design: As shown in FIG. 4, the piezoelectric material 42 on the base 41 is stacked with a mass 43 to be independent of the external cover 44 for dealing with the influence of the sonic vibration;

5) Mushroom design: As shown in FIG. 5, the base 51 attaches thereon a beam 52 which has two free ends and is coated thereon with a piezoelectric material 53 serving as the sensing element.

Basic structural designs of all the above piezoelectric accelerometers are point sensors which measure the acceleration by the electronic signal generated when the strain of the piezoelectric material is subjected to change. No matter whichever sensor design is concerned, purposes of superior dynamic response and broadened system bandwidth are always sought. The bottleneck of the conventional point accelerometer is that the integral system bandwidth of the accelerometer is limited by the resonant mode of the sensor structure. If a better bandwidth is sought by raising the first resonant mode frequency, the accelerometer will have a poor dynamic response to the low frequency. If the structural stiffness of the accelerometer structure is reduced to increase the dynamic response to lower frequencies, the bandwidth of the accelerometer will be lowered.

Alternatively, if the acceleration signal of a specific frequency is to be measured, the conventional method is to provide a filter with the electronic circuit for attenuating the accelerometer signal of undesirable bandwidths. Since this filter modulates signal on the time domain, it must follow the causality. According to the Bode Gain Phase Theorem, phase change of the original acceleration signal will be introduced so that there will be an extreme difference between the measured acceleration signal and the real acceleration signal, which requires an additional compensation to calibrate the measured signal. It is not wonderful in use.

It is therefore tried by the Applicant to deal with the above situations encountered in the prior art.

SUMMARY OF THE INVENTION

It is therefore an object of the present invention to provide a vibration measuring device for accurate measurement in a specific bandwidth.

It is further an object of the present invention to provide a vibration measuring device for selective accurate measurement in a frequency range.

It is further an object of the present invention to provide a vibration measuring device utilizing a feedback control loop to moderate the deformation of sensing structure.

It is still an object of the present invention to provide an accelerometer having an increased bandwidth and a reduced bulk.

It is additional an object of the present invention to provide a point distributed piezoelectric sensor by gathering together advantages of distributed sensor and point sensor.

It is yet an object of the present invention to provide a sensor of spatial filtering function having the modulated gain without the influence on the phase angle.

It is furthermore an object of the present invention to provide a spatial filter which will not result in any unnecessary phase lag but has a freely selective bandwidth.

It is again an object of the present invention to provide a modal sensor which can lift the bandwidth limitation resulting from the sensing structure resonance through the manufacture of the higher modal sensor and raising the bandwidth to an even higher mode.

According to an aspect of the present invention, a vibration measuring device for measuring a vibration of an object includes a sensing body generating a dynamic information in response to the vibration, and a piezoelectric sensing layer disposed on the sensing body to construct thereby a sensor and formed in a distributed mode to measure the dynamic information in a selected specific bandwidth.

Certainly, in the vibration measuring device, the sensor can be a point sensor, the object is one selected from a group consisting of building structure, sound equipment and military mechanics, the sensing body is a sensor structure body, and the piezoelectric layer has an effective piezoelectric profile.

Certainly, the present vibration measuring device can be an accelerometer, a device for metering acceleration rate or a force sensor. The accelerometer, metering device and force sensor can respectively have sensor structure bodies respectively having different dynamic informations.

Preferably the sensing layer includes two piezoelectric sheets oppositely adhered with each other and respectively having two piezoelectric surfaces for sensing in the specific bandwidth, in which the two piezoelectric surfaces respectively adhere thereto two surface electrodes collectively forming an effective surface electrode for generating the effective piezoelectric profile.

Preferably the two piezoelectric sheets are oppositely polarized in the effective surface electrode and have an electromagnetic interference shielding effect through a pseudo ground.

Preferably the sensing layer has polarized profile and direction through a potential difference. The potential difference of the sensing layer results in a sensing charge along a thickness of the sensing layer, and the sensing charge being a charge signal in the effective surface electrode is to be measured by the effective surface electrode.

Preferably the effective surface electrode has a specific shape determined by a surface electrode function for determining the specific shape in response to the respective sensing body. The surface electrode function is a weighting function, and the charge signal is presented by a frequency spectrum and modulated by the weighting function. The surface electrode function cooperates with a Heaviside step function for reducing a leaking phenomenon of the frequency spectrum.

Preferably the measuring device is a sensor system, the vibration of the object is revealed by a number of waves in the space domain, and an integration of the surface electrode in the space domain can overcome a phase delay phenomenon of the space waves resulting from a modulated gain of the sensor system in time domain. The phase angle of the space waves is kept constant for simultaneously obtaining past, present and future information of the space waves in order that the measuring device serves as a spatial filter of broad bandwidth or selective bandwidth. The surface electrode function is a Laplace transform function for selecting a filtering effect and facilitating a connection with a control loop.

Preferably the piezoelectric sensing layer is a mode 1 sensor being a matching filter of the sensing body. The present vibration measuring device preferably further includes a second sensor for a broader bandwidth. The second sensor is determined by a second surface electrode function for eliminating a sensitivity with respect to the mode 1 sensor and the second surface electrode function is obtained through expansion from an eigen function so that the second sensor is an anti-mode 1 sensor. The anti-mode 1 sensor has a surface electrode having an inverse polarity with respect to the mode 1 sensor, and has a vertically symmetrical shape for increasing a profile of the charge signal. The anti-mode 1 sensor can cancel an error signal resulting from twisting if the measuring device has a undesired resonant frequency, and the sensing body is a flexible structure for reducing a bulk thereof and raising a low frequency response effect thereof. The anti-mode 1 sensor can be manufactured by a semiconductor procedure, and the measuring device can be a point distributed sensor serving as a low frequency accelerometer.

Generally the effective piezoelectric profile of the piezoelectric sensing layer can vary with a polarization modulation of the piezoelectric sensing layer made of piezoelectric polymer of polyvinylidene fluoride (PVDF), lead zirconate titanate (PZT) or zinc oxide (ZnO).

The selected specific bandwidth can be a frequency domain of low-pass, high-pass, band-pass or band-stop. The present vibration measuring device further includes a second piezoelectric sensing layer for measuring the dynamic information in a second selected bandwidth.

Preferably the present measuring device is an accelerometer, the piezoelectric sensing layer senses the dynamic information to generate an electric charge or a voltage signal and is electrically connected to an interface circuit, and the interface circuit is provided with an amplifier for amplifying the electric charge or the voltage signal to obtain an acceleration signal.

Alternatively, the present vibration measuring device can be a device for metering an acceleration rate, the piezoelectric sensing layer senses the dynamic information to generate a current signal and is electrically connected to an interface circuit, and the interface circuit is provided with an amplifier for amplifying the current signal to obtain an acceleration rate signal.

Certainly, the sensing body can be a beam or a shaft. The present vibration measuring device further includes an actuator connected to the sensing body, and a feedback circuit electrically connected to the piezoelectric sensing layer and the actuator for receiving a measured signal produced by the piezoelectric sensing layer and transmitting a feedback signal to the actuator for controlling a deformation of the sensing structure.

Alternatively the present measuring device can be an active point distributed sensor, and the feedback circuit includes an interface circuit, a feedback compensation circuit and an amplifier, in which the feedback compensation circuit outputs the measured signal proportional to the feedback signal.

Certainly, the piezoelectric sensing layer can be a mode sensor in order that the measuring device serves as an active point distributed sensor of a relatively specified frequency sensitivity, or an anti-mode sensor in order that the measuring device serves as an active point distributed sensor of a relatively specified rejected frequency sensitivity. The present measuring device can be an accelerometer, a device for metering acceleration rate or a force sensor.

Certainly, the feedback circuit can include a proportion/integration/differentiation (PID) controller, and a phase lag compensator or a phase lead compensator. The actuator can be a film actuator made of polyvinylidene fluoride (PVDF) or lead zirconate titanate (PZT), or a point actuator made of polyvinylidene fluoride (PVDF) or lead zirconate titanate (PZT) and driven by an electric field, a magnetic field or an electromagnetic field, or a distributed actuator driven by an electric field, a magnetic field or an electromagnetic field.

According to another aspect of the present invention, a vibration measuring method for measuring a vibration of an object includes steps of providing a sensing body generating a dynamic information in response to the vibration, and providing a piezoelectric sensing layer formed in a distributed mode to measure the dynamic information in a selected specific bandwidth.

Preferably the present vibration measuring method further includes steps of providing an actuator, and providing a feedback circuit for receiving a measured signal produced by the piezoelectric sensing layer and transmitting a feedback signal to the actuator for controlling a deformation of the sensing structure.

The present invention may best be understood through the following descriptions with reference to the accompanying drawings, in which:

DETAILED DESCRIPTION OF THE PREFERRED EMBODIMENTS

Figure 1:
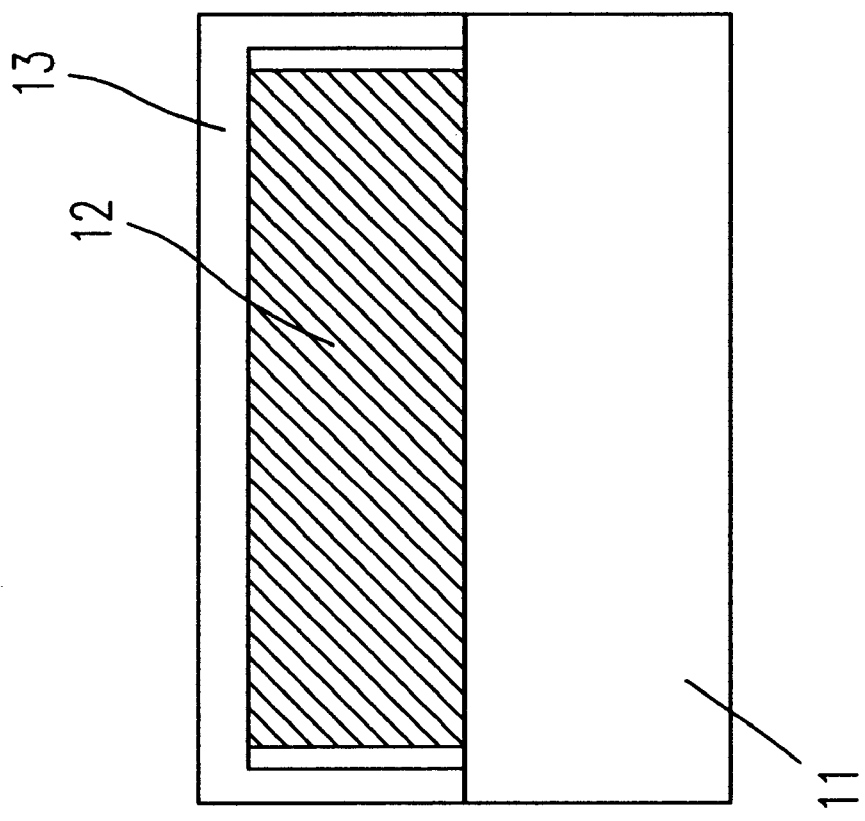
FIG. 1 is a schematically sectional view showing a compression accelerometer according to the prior art.
Figure 2:
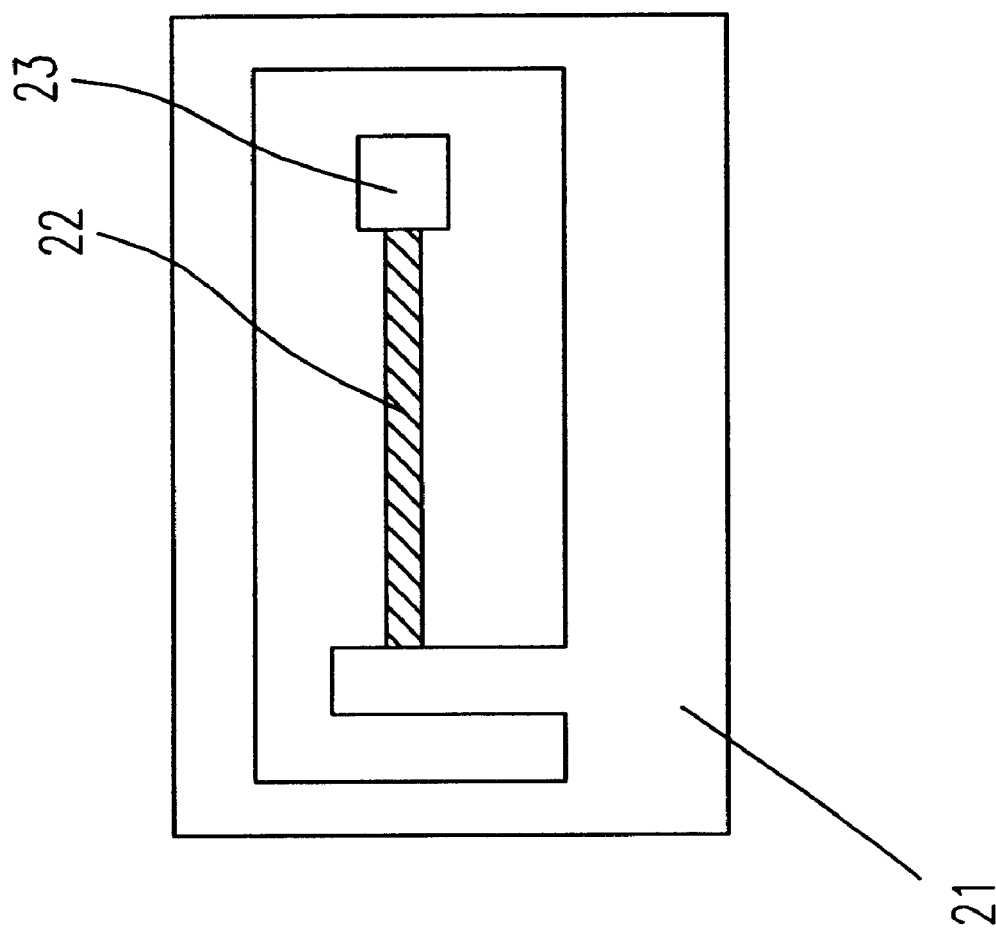
FIG. 2 is a schematically sectional view showing a cantilevered piezoelectric accelerometer according to the prior art.
Figure 3:
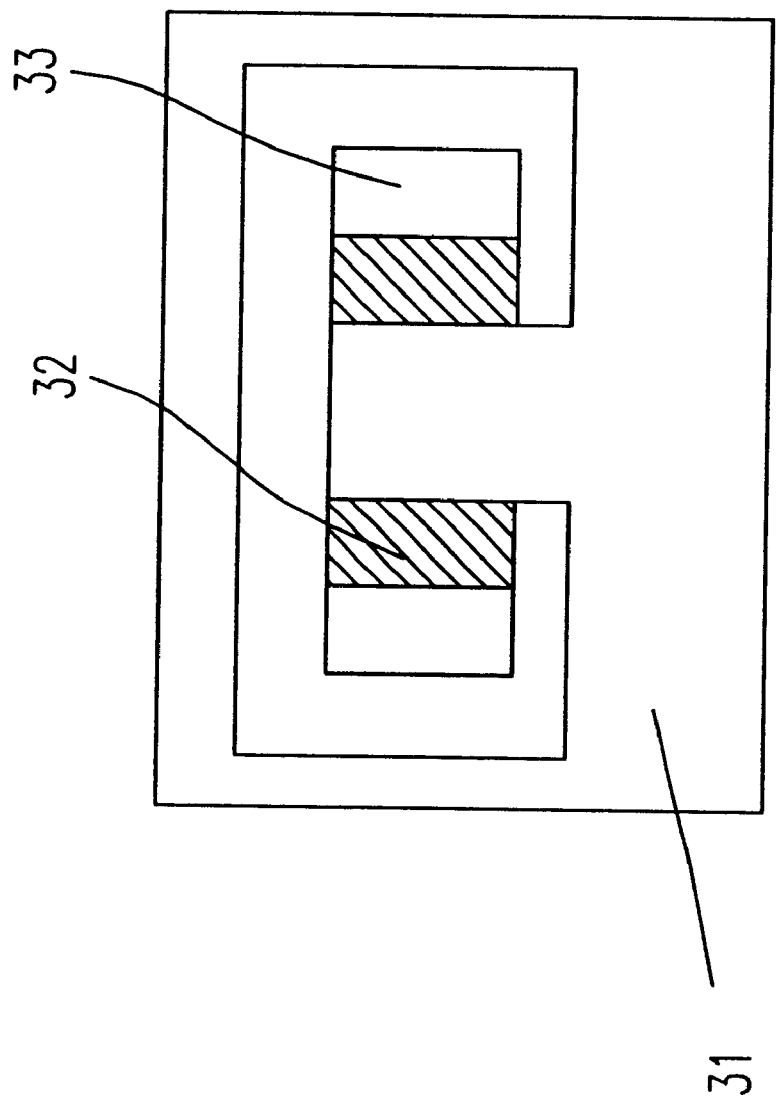
FIG. 3 is a schematically sectional view showing a shear piezoelectric accelerometer according to the prior art.
Figure 4:
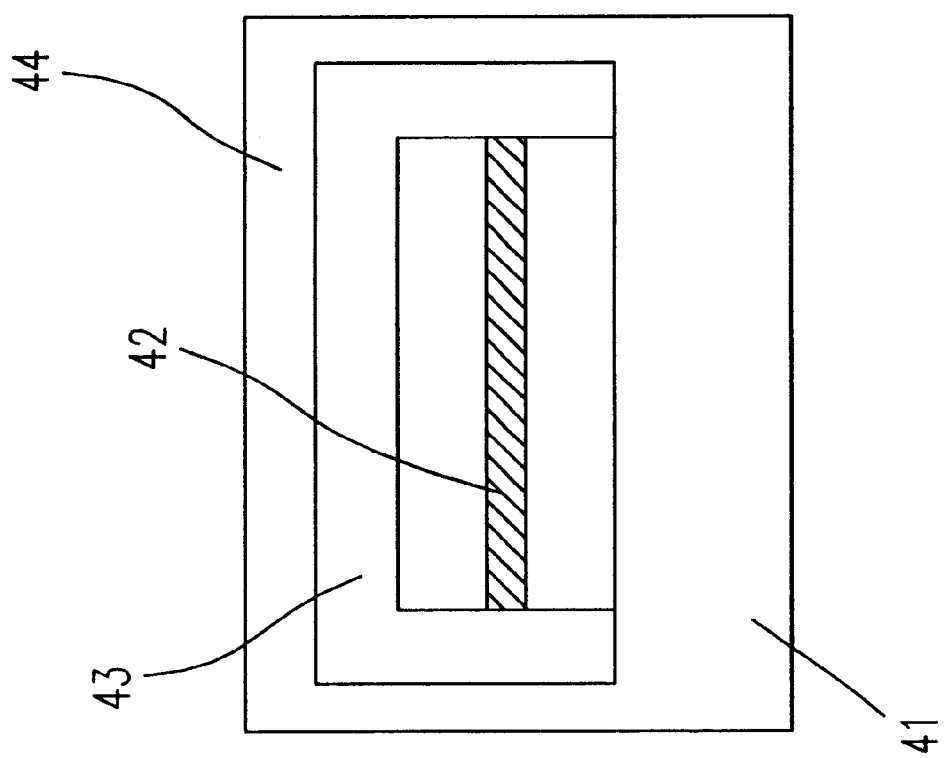
FIG. 4 is a schematically sectional view showing a single ended compression accelerometer according to the prior art.
Figure 5:
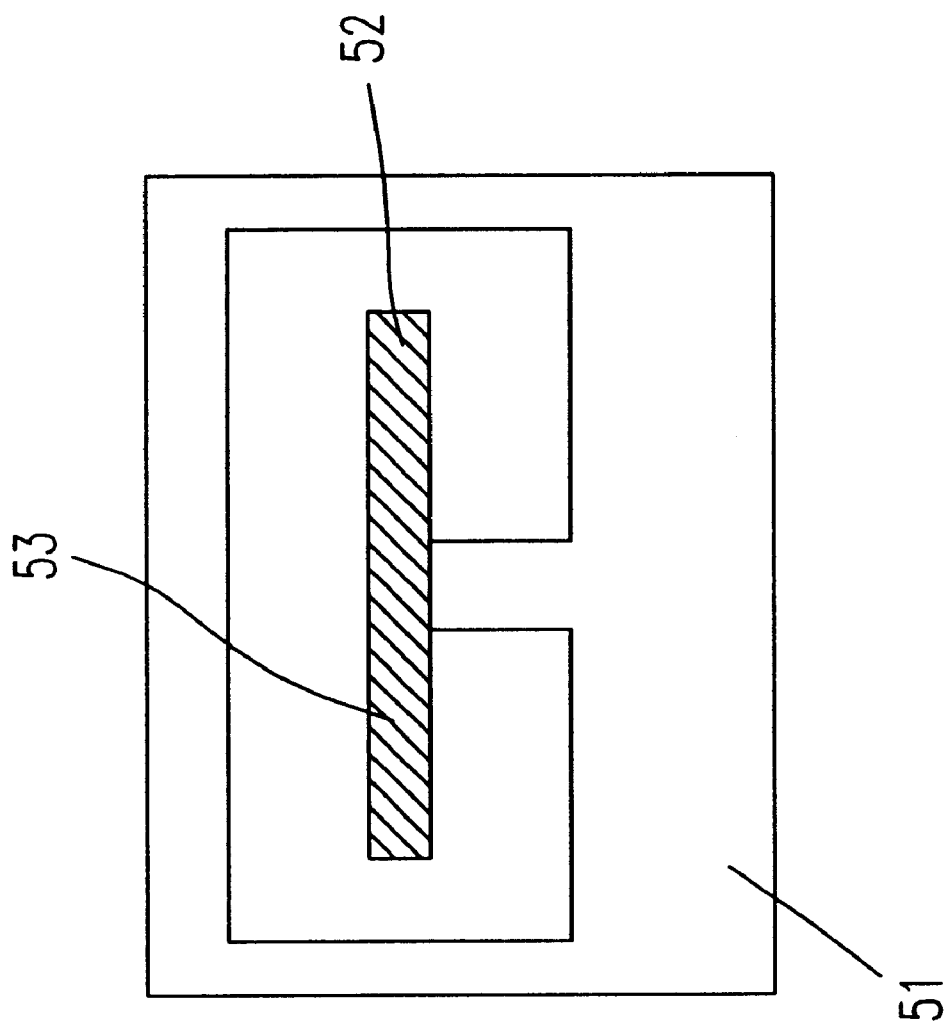
FIG. 5 is a schematically sectional view showing a mushroom piezoelectric accelerometer according to the prior art.
Figure 6A:
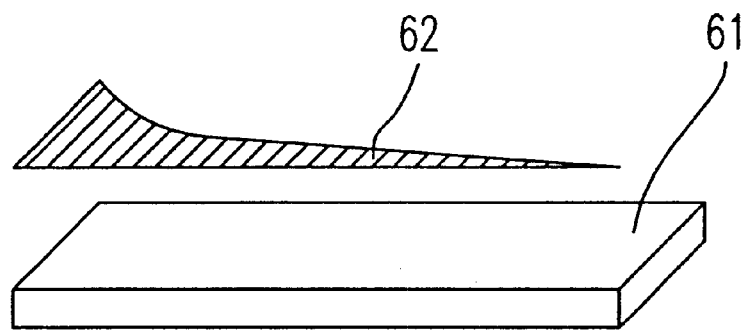
FIGS. 6A and 6B are respectively partially exploded and perspective schematical views showing a preferred embodiment of a vibration measuring device according to the present invention.

As shown in FIG. 6, there is shown a vibration measuring device 60 for measuring a vibration of an object, which includes a sensing body 61 generating a dynamic information in response to the vibration, and a piezoelectric sensing layer 62 disposed on sensing body 61 to construct thereby a distributed sensor and formed a point sensor to measure the dynamic information in a selected specific bandwidth. The object can be building structure, sound equipment or military mechanics, sensing body 61 can be a sensor structure body, and piezoelectric sensing layer 62 being a thin film has an effective piezoelectric profile. The present vibration measuring device 60 can be an accelerometer, a device for metering acceleration rate or a force sensor which have respective sensor structure bodies 61 respectively having different dynamic informations.

Thin piezoelectric sensing layer 62 has a surface, a thickness and a specific shape for sensing in the specific bandwidth and generating a polarization phenomenon including a polarized profile and a polarized orientation. Piezoelectric sensing layer 62 is made of piezoelectric polymer of polyvinylidene fluoride (PVDF), lead zirconate titanate (PZT) or zinc oxide (ZnO).

The selected specific bandwidth for piezoelectric sensing layer 62 can be a frequency domain of low-pass, high-pass, band-pass or band-stop. When the present measuring device 60 is an accelerometer, piezoelectric sensing layer 62 senses the dynamic information to generate an electric charge or a voltage signal and is electrically connected to an interface circuit 63 which is provided with an amplifier 64 for amplifying the electric charge or the voltage signal to obtain an acceleration signal.

If the present measuring device 60 is a device for metering an acceleration rate, piezoelectric sensing layer 62 senses the dynamic information to generate a current signal and is electrically connected to the interface circuit 63 which is provided with the amplifier 64 for amplifying the current signal to obtain an acceleration rate signal.

Figure 6B:
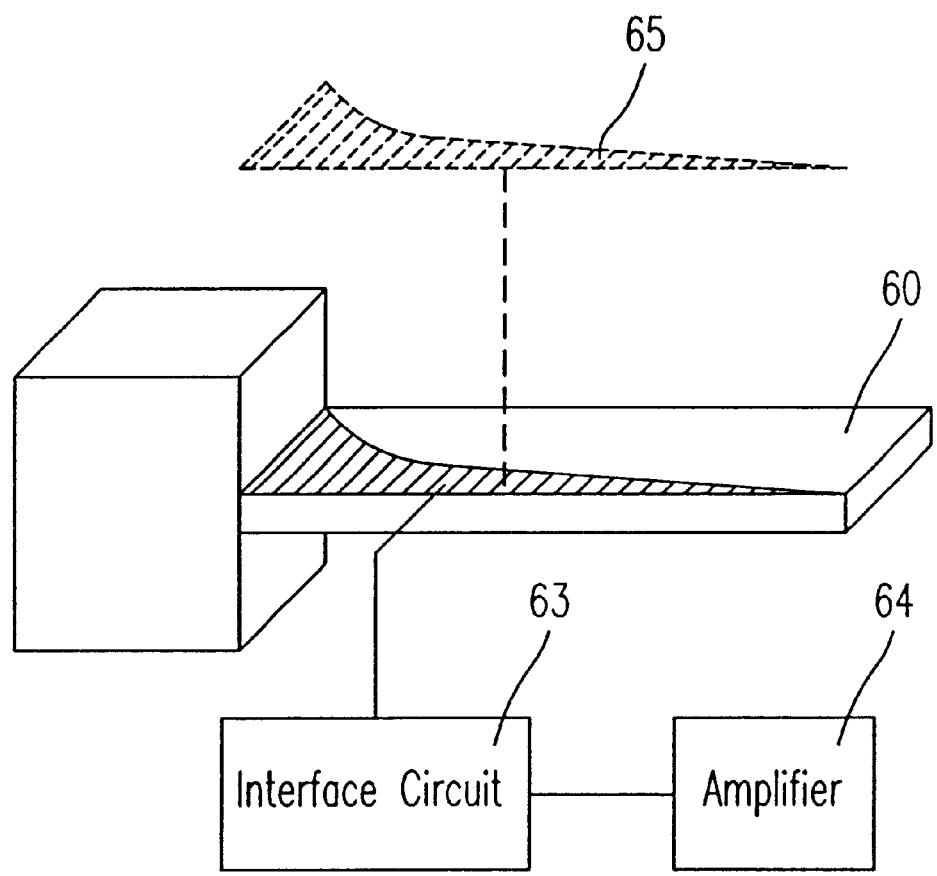
Figure 9:
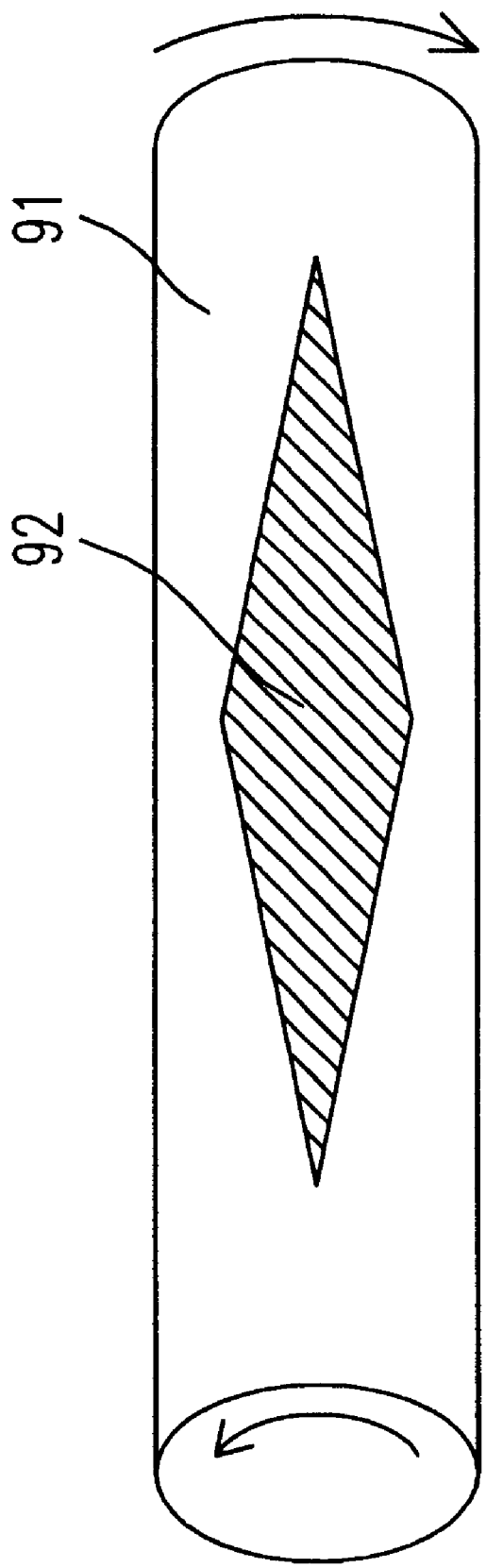
FIG. 9 is a schematical view showing another preferred embodiment of a vibration measuring device according to the present invention.

The present vibration measuring device 60 could further include a second piezoelectric sensing layer 65 for measuring, through the linear addition principle, the dynamic information in a second selected bandwidth. Sensing body 61 can be a beam as shown in FIG. 6B or a shaft 91 as shown in FIG. 9 having thereon a distributed piezoelectric sensing layer 92.

Figure 11:
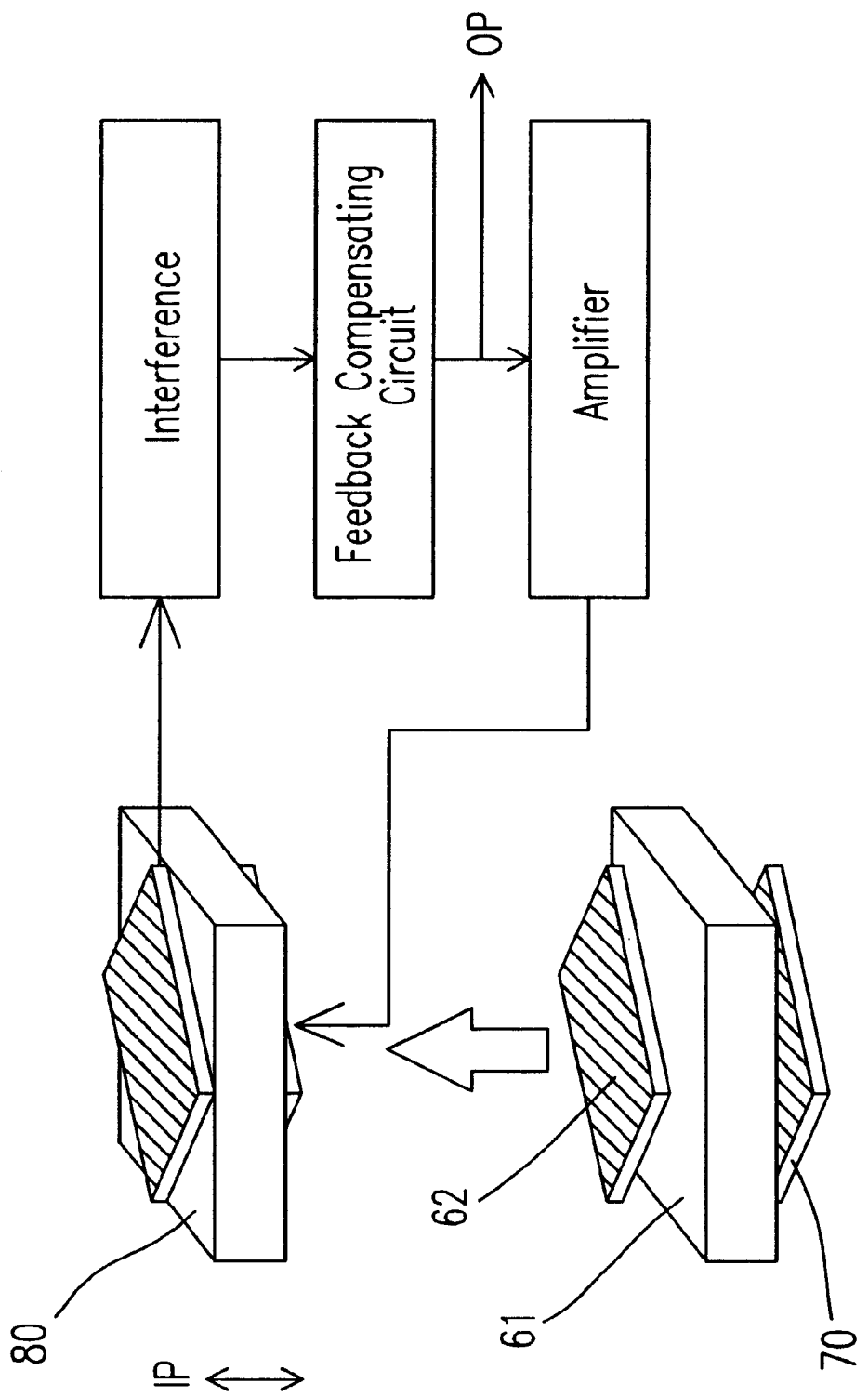
FIGS. 11, 11A and 11B are partially exploded and perspective schematical views showing a further preferred embodiment of a vibration measuring device according to the present invention.
Figure 11A:
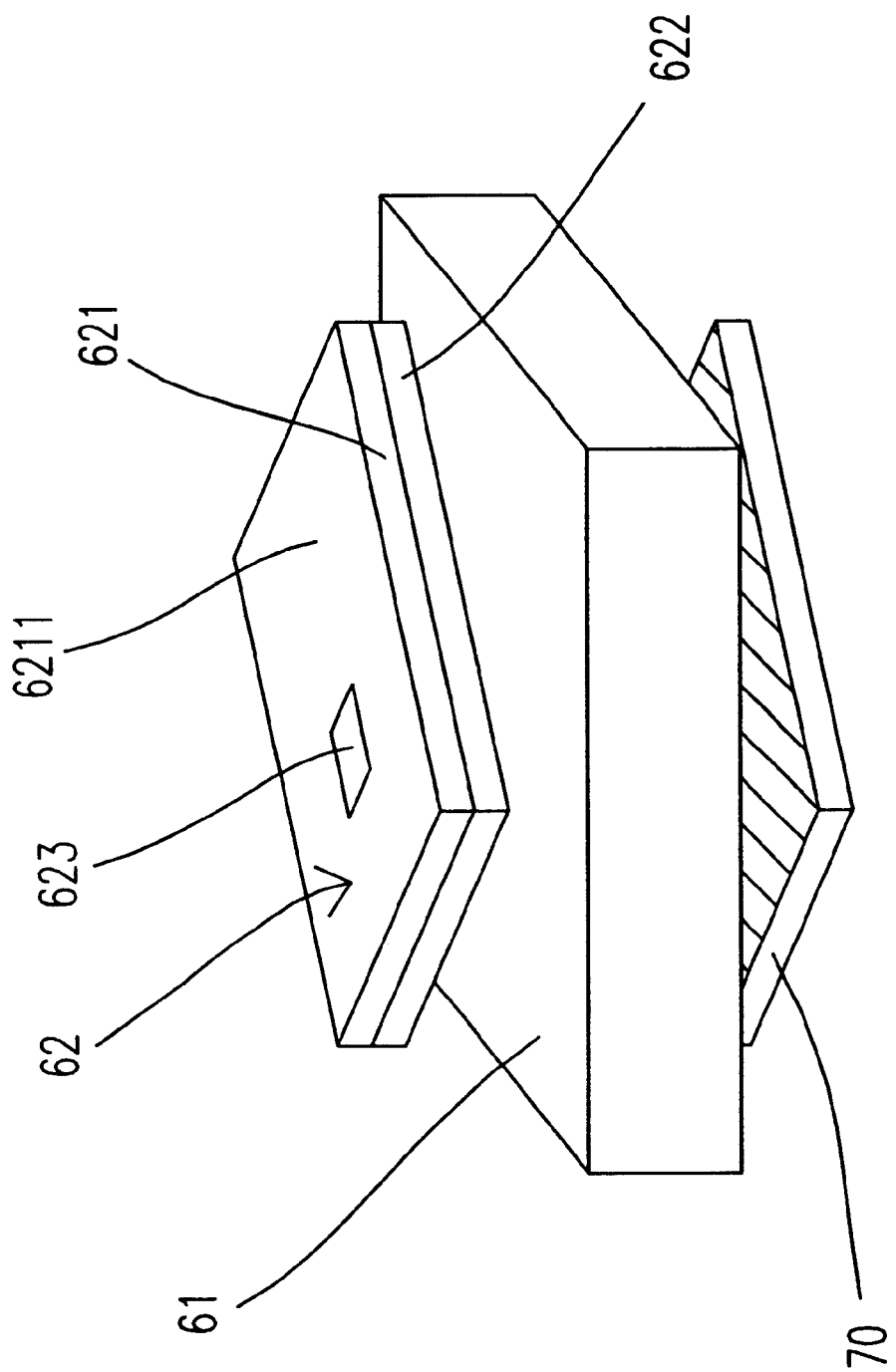

As shown in FIG. 11, the present vibration measuring device 60 further includes an actuator 70 connected to sensing body 61 to form an active sensor system 80, and a feedback circuit 88 electrically connected to piezoelectric sensing layer 62 and actuator 70 for receiving a measured signal produced by piezoelectric sensing layer 62 and transmitting a feedback signal to actuator 70 for controlling the deformation of sensing body 61.

The present measuring device 60 can be an active point distributed sensor and can be an accelerometer, a device for metering acceleration rate or a force sensor as mentioned hereinbefore. Feedback circuit 88 includes an interface circuit 81, a feedback compensation circuit 82 and an amplifier 83, in which feedback compensation circuit 82 outputs the measured signal proportional to the feedback signal and includes a proportion/integration/differentiation (PID) controller and a phase lag compensator or a phase lead compensator. Actuator 70 can be a thin film actuator made of polyvinylidene fluoride (PVDF) or lead zirconate titanate (PZT). Certainly, actuator 70 can be a point or distributed actuator driven by an electric field, a magnetic field or an electromagnetic field.

For implementing a vibration measurement according to the present invention, the method for measuring a vibration of an object includes steps of providing a sensing body 61 generating a dynamic information in response to the vibration, and providing a piezoelectric sensing layer 62 formed in a distributed mode to measure the dynamic information in a selected specific bandwidth. Such method preferably further includes steps of providing an actuator 70, and providing a feedback circuit 88 for receiving a measured signal produced by piezoelectric sensing layer 62 and transmitting a feedback signal to actuator 70 for controlling a deformation of sensing body 61.

Since the piezoelectric ceramics cannot subject to tension and large bending moment, it is improper to be used as the point distributed sensor 60 as shown in FIG. 6 showing a cantilevered beam 61 serving as the basic structure of sensor and adhering thereon piezoelectric sensing layer 62 designed with the surface electrode. The piezoelectric polymer, e.g. PVF2 (i.e. PVDF), is typically a flexible polymer, has a high piezoelectric constant and can endure deformation, high pressure and high tension. Although its coupling factor and dielectric constant are not so outstanding as those of the piezoelectric ceramics, it is suitable for the demand of piezoelectric sensor or sensing layer 62. Among numerous piezoelectric polymers, PVF2 of extremely high piezoelectric constant is selected to testify its appropriateness for use in the point distributed piezoelectric accelerometer.

The basic design method hereinafter described can equally apply to all piezoelectric materials and piezoelectric manufacturing process. To design with the concept of the distributed sensor, specific sensor structures different from sensor structure 61 in FIG. 6 can be used to design sensors of different bandwidths.

By using the spatial filter, the point distributed piezoelectric accelerometer can be used to achieve effects of modulating the gain and keeping the phase angle constant. Further, such space distributed design concept can be put into applications of various point sensors, e.g. force sensor or capacitance sensor as will be described in the following.

The point distributed (POD) sensor in fact is a point sensor but is designed with the concept of the space distributed sensor in order that the sensor can select the measured frequency domain for serving as any specific sensor of low-pass, high-pass, band-pass or band-stop whose phase does not change with causality. Such sensor can measure external dynamic informations of different frequency domains or measure physical characteristics of acceleration or acceleration rate of an external system according to different interface circuits.

The present distributed piezoelectric sensing layer 62 can introduce spatial parameters into the dynamic information to be measured and the present sensor can be designed using how the effective piezoelectric profile of the piezoelectric sensing layer is distributed in the spatial wave number domain as a designing parameter so that the design requirement of frequency response can be met by the mutually corresponding dispersion relation between the spatial wave number domain and the frequency domain.

The present piezoelectric sensing layer distributed in the spatial wave number domain can be treated as simultaneously collecting past, present and future information of the space waves in order that the present sensor can break the limitations of causality and Bode gain phase theorem to achieve the effect of an ideal filter whose gain of system transfer function can be modulated without resulting in a phase shift. The present vibration measuring device can easily be achieved by skillfully gathering together advantages of conventional point sensor and distributed sensor.

Theoretical bases of the present invention can be summarized as in the following 7 items:

1) Basic Equations of Piezoelectric Thin Film 62

Basic equations of the piezoelectric sensing layer can be expressed in forms of stress and strain as follows: (Lee et al., 1989)

$$T_p = c_{pq}^E S_q - e_{kp} E_k, \quad (1)$$

$$D_i = e_{iq} S_q + \epsilon_{ik}^s E_k, \quad (2)$$

or $$S_q = s_{pq}^E T_q + d_{kp} E_k, \quad (3)$$

$$D_i = d_{iq} T_q + \epsilon_{ij}^T E_k, \quad (4)$$

wherein the lower indices i, j or k=1~3, p or q=1~6, $T_p$ is stress, $S_q$ is strain, $E_k$ is electric field, $D_i$ is potential difference, and $C_{pq}$, ij, $S_{pq}=(C_{pq})-1$, $e_{kp}$ and $d_{ip}$ respectively stand for elastic stiffness matrix, permittivity matrix, elastic compliance matrix, piezoelectric stress matrix and piezoelectric strain matrix. Definitions of the above indices all follow IEEE (Institute of Electrical and Electronics Engineers) compact matrix notation (ANSI (American National Standards Institute)/IEEE, 1987). Through symmetry of the piezoelectric sensing layer, it can be known the piezoelectric strain constant will be 0 in some specific directions.

The piezoelectric material of PVF2 follows mm2 symmetry (mirror mirror 2 fold symmetry, which means that the material itself has mirror symmetry in either X- or Y-axes, and also has symmetry in Z-axis after rotated 180°. The piezoelectric strain constant dip matrix can be expressed as follows:

$$d_{ip} = \begin{bmatrix} 0 & 0 & 0 & 0 & d_{15} & 0 \\ 0 & 0 & 0 & d_{24} & 0 & 0 \\ d_{31} & d_{32} & d_{33} & 0 & 0 & 0 \end{bmatrix}, \quad (5)$$

The Kirchhoff hypothesis points out (Ashton et al., 1969): If (1) $T_3 \ll T_1$, $T_2$, and (2) the plane, before deformed, perpendicular to the mid-plane keeps perpendicular to the mid-plane after deformed, the shear stresses $T_4$, $T_5$ can be ignored. If Kirchhoff hypothesis is tenable, it can be derived that the relevant sheet plate is subject to a plane stress state. Accordingly, a thin layer in a laminated structure can be supposed to be subject to a plane stress state.

After modifying equations (3) and (4) to be adapted under the plane stress state, we obtain (Lee, 1987):

$$\begin{bmatrix} S_1 \\ S_2 \\ S_3 \end{bmatrix} = \begin{bmatrix} 1/Y & -v/Y & 0 \\ -v/Y & 1/Y & 0 \\ 0 & 0 & 2(1+v)/Y \end{bmatrix} \begin{bmatrix} T_1 \\ T_2 \\ T_6 \end{bmatrix} + \begin{bmatrix} d_{31}E_3 \\ d_{32}E_3 \\ 0 \end{bmatrix}, \quad (6)$$

and $$D_3 = \epsilon_{33}E_3 + d_{31}T_1 + d_{32}T_2, \quad (1)$$

wherein Y represents Young's modulus and v represents Poisson's ratio. It is to be noticed that equation (6) is of the same type as that for the isotropic material. Although it has been proven that the piezoelectric property cannot exist in the isotropic material (Cady, 1964), PVF2 can still be represented by the above equation if the Young's modulus of the piezoelectric material is much smaller that of the structure. Thus, even if constant Y is referred to the coefficient of the structure rather than that of the piezoelectric thin layer, it still is reasonable to use the above equation for simulating the thin layer of non-isotropic piezoelectric material. Equation (6) can be expressed through inverse operation in the form similar to Equation (1) as follows:

$$\begin{bmatrix} T_1 \\ T_2 \\ T_6 \end{bmatrix} = [c] \begin{bmatrix} S_1 \\ S_2 \\ S_6 \end{bmatrix} - [c] \begin{bmatrix} d_{31}E_3 \\ d_{32}E_3 \\ 0 \end{bmatrix}, \quad (8)$$

wherein [c] is a stiffness matrix made by using principal axes X', Y', Z' of a single thin layer as reference axes and can be expressed as follows:

$$[c] = \begin{bmatrix} Y/(1-v^2) & vY/(1-v^2) & 0 \\ vY/(1-v^2) & Y/(1-v^2) & 0 \\ 0 & 0 & Y/2(1+v) \end{bmatrix}, \quad (9)$$

Accordingly, basic laminate equations generally only having E3 electric field can be expressed as follows:

$$\begin{bmatrix} T_1 \\ T_2 \\ T_6 \end{bmatrix} = [c] \begin{bmatrix} S_1 \\ S_2 \\ S_6 \end{bmatrix} - [c] \begin{bmatrix} d_{31}E_3 \\ d_{32}E_3 \\ 0 \end{bmatrix}, \quad (10)$$

and $$D_3 = \epsilon_{33}E_3 + d_{31}T_1 + d_{32}T_2, \quad (11)$$

By assuming the piezoelectric coefficient diq in the above equation to be zero, basic equations of the thin layer having no piezoelectric effect can be obtained.

2) Equations of piezoelectric sensor

The property of piezoelectric sensing layer follows the basic equation (11) with polarized profile through the direction along the thickness of the sensing layer. The potential difference of thickness of sensing layer results in a sensing charge. The sensing charge is a charge signal in the effective surface electrode which is adhered on the sensing layer with a specific shape determined by a surface electrode function for determining the specific shape in response to the respective sensing body. Certainly, the signal measured by the piezoelectric sensing layer is also related to the information of the sensing body structure. In the case of a single piezoelectric thin layer, polarized axial directions of the piezoelectric thin layer will be the same as those of three axes of a lamination. By using the theory of linear elastic material mechanics, the strain and deformation relationship of an Euler beam can be showed as follows:

$$\begin{bmatrix} S_1 \\ S_2 \\ S_6 \end{bmatrix} = \begin{bmatrix} S_1^0 \\ S_2^0 \\ S_6^0 \end{bmatrix} + z \begin{bmatrix} k_1 \\ k_2 \\ k_6 \end{bmatrix} = \begin{bmatrix} \partial u_0/\partial x \\ \partial v_0/\partial y \\ \partial u_0/\partial y + \partial v_0/\partial x \end{bmatrix} + z \begin{bmatrix} -\partial^2 w/\partial x^2 \\ -\partial^2 w/\partial y^2 \\ -\partial^2 w/\partial x \partial y \end{bmatrix}, \quad (12)$$

wherein u, v, w respectively represent deformations on X-, Y- and Z-axes, in which w stands for the transverse displacement of the Euler beam, and the upper index 0 stands for strain and deformation in the neutral plane. After the stress-and-deformation relationship obtained from equations (12) and (10) is taken into equation (11), through the use of equation of the piezoelectric constant relationship, $e_{ip} = d_{iq}c^E_{qp}$, the equation for the piezoelectric sensor of single layer can be obtained as follows:

$$D_3 = \epsilon_{33} + e_{31}(S_1^0 + zk_1) + e_{32}(S_2^0 + zk_2) + e_{36}(S_6^0 + zk_6), \quad (13)$$

wherein $e_{ip}$ is a function of x, y with different polarized piezoelectric material or its repolarization so that the parameter $P_p(x, y)$ can be introduced to represent the polarized direction and profile, that is, $e_{ip} = e^0_{ip}P_p$ where $e^0_{ip}$ is a constant. Applying the Gauss' Law, the signal obtainable through the surface electrode is as follows:

$$q(t) = \int_S \underline{D} \cdot d\underline{\sigma} \quad (14)$$

wherein $\underline{D}$ is the vector of the potential difference, and $d\underline{\sigma}$ represents the normal vector of every area element $\overline{S}$. In addition, since the dielectric will permanently keep its electrical neutrality, the direct integration of equation (14) for the piezoelectrical material will always be zero so that the integration range in the Z-direction will be from the half height to the surface electrode for the piezoelectric material of single layer. The equivalent circuit of the piezoelectric material can be regarded as a capacitor for storing the charge under the mechanical field. The potential difference it generates in the thickness direction can be expressed as $\underline{D} = D_3 \cdot \underline{e}_3$ where $\underline{e}_3$ is a unit vector parallel to the Z-axis. It can be known from the equivalent circuit that only when the circuit is a closed loop, the sensed charge can be measured. Specifically, the potential difference signal can be measured only at where both upper and lower surface electrodes are coated with the piezoelectric material.

Specifically, the intersection of sets of upper and lower surface electrodes, $S^{(12)} = S^1 \cap S^2$, can be regarded as the effective surface electrode. Only signals in this effective surface electrode can be measured. Since our main purpose is to manufacture a structural vibration sensor for measuring the charge signal produced by the mechanical energy, the electric field $E_3$ must be set to be zero. In the experiments, the sensing layer 62, as shown in FIG. 11, includes two oppositely polarized piezoelectric sheets 621, 622 oppositely adhered with each other and respectively having two piezoelectric surfaces 6211 respectively adhering thereto two surface electrodes 623 collectively forming the effective surface electrode for generating the effective piezoelectric profile. The two piezoelectric sheets 621, 622 build up an electromagnetic interference (EMI) shielding effect after grounded. After the signal can be obtained through a charge or current amplifier, $E_3$ can be defined as zero through a pseudo ground. After taking equation (13) and the strain-and-displacement relation into equation (14), the piezoelectric thin layer sensor equation can now be expressed as follows:

$$q(t) = \int\int_{\delta(12)} \left[ e_{31}\frac{\partial u_0}{\partial x} + e_{32}\frac{\partial v_0}{\partial y} + e_{36}\left(\frac{\partial u_0}{\partial y} + \frac{\partial v_0}{\partial x}\right) \right] dxdy - \tag{15}$$
$$z^0 \int\int_{\delta(12)} \left[ e_{31}\frac{\partial^2 w}{\partial x^2} + e_{32}\frac{\partial^2 w}{\partial y^2} + 2e_{36}\frac{\partial^2 w}{\partial xy} \right] dxdy,$$

wherein $Z^0$ is the location of the piezoelectric thin film center. Furthermore, if the piezoelectric sensor is a piezoelectric laminate sensor composed of piezoelectric sensing layers, the sensor equation can be derived by using IEEE indices and composite laminate theory, starting from the above equation.

Taking an Euler beam having width b and length a as an example, axial stresses in X- and Y-axes are far smaller than the flexible stress in the Z-axis so that $u_0=v_0=0$ in equation (16). Assuming that the transverse displacement is not dependent on the Y- axis, that is, w=w(x, t), equation (15) can be simplified as follows:

$$q(t) = -z^0 e_{31}^0 \int_0^a \varsigma(x)\frac{\partial^2 w}{\partial x^2} dx, \quad \text{wherein} \tag{16}$$

$$\varsigma(x) = \int_{-b/2}^{b/2} F(x,y) P_1(x,y) dy, \tag{17}$$

is a function of the effective surface electrode. F(x, y) is a function describing the distribution of the effective surface electrode. $P_1(x, y)$ represents polarized direction and profile of $e_{31}$ as above described, and the polarized profile changes with the thickness of piezoelectric thin layer 62. The above two equations are basic sensor equations of the present invention and can be the basis for developing a series of piezoelectric sensors.

3) Spatial Filter

To design with the effective surface electrode function for the piezoelectric sensor, a weighting function is introduced on the spatial wave number domain, and the relevant charge signal is presented by a frequency spectrum and modulated by the weighting function. Specifically, the present measuring device can be a sensor system, in which the vibration of the object is reflected by a number of waves in the sensing space, and integration of the surface electrode in the sensing space can overcome a phase delay phenomenon of the space waves resulting from a modulated gain of the sensor system. The phase delay phenomenon is the reason why the bandwidth of conventional sensors is limited from one fifth to one tenth of that in the first resonant mode of the sensor structure. For the spatial wave number domain, past, current and future informations can simultaneously be obtained through the integration of spatial wave number domain. Accordingly, the signal measured by sensor designed with such concept will not subject to the influence of causality and thus a spatial filter can be developed around Bode gain phase theorem (Miller, 1990). Through use of the spatial filter technique and introduction of the design parameter of the effective surface electrode function of the piezoelectric sensor, sensors of broad or even selective bandwidth can be obtained.

As to an Euler beam without damping, the governing equation of the system movement can be described as follows: (Graff, 1975):

$$EI\frac{\partial^4 w(x,t)}{\partial x^4} + \rho A\frac{\partial^2 w(x,t)}{\partial t^2} = 0, \tag{18}$$

wherein EI stands for the stiffiess constant, A for cross-sectional area of beam, and σ stands for density. Assuming the time simple harmonic signal $w(x, t)=w(x)e^{iwt}$ in time domain, the above equation can be simplified as follows:

$$\frac{\partial^4 w(x)}{\partial x^4} - k^4 w(x) = 0, \tag{19}$$

wherein k stands for the wave numbers $$k^4 = \frac{\rho A}{EI}\omega^2, \tag{20}$$

expressing the dispersion relationship wherein ω represents for the frequency, having the following general solution:

$$w(x,t)=[w_{lp}e^{ikx}+w_{le}e^{kx}+w_{rp}e^{-ikx}+w_{re}e^{-kx}]e^{i\omega t}, \tag{21}$$

wherein $w_{rp}$, $w_{lp}$, $w_{re}$, $w_{le}$ respectively stand for wave mode amplitudes, the subscripts lp represents the leftward propagating wave having an energy independent of the propagating distance, and the subscripts re represents the rightward evanescent wave having an energy exponentially decreasing with the boundary condition. It is to be noticed that for the electromagnetic wave, the piezoelectric material has similar governing equation. Since there are extremely difference between magnitudes of structural frequency and the electromagnetic frequency, the influence of the electromagnetic wave on the signal obtainable from the piezoelectric sensor will not be discussed here. The boundary conditions of a fixed-free beam are one end fixed and the other end free so that if the vibration source is inputted from the fixed end in a simple harmonic oscillation way, the boundary conditions can be expressed as follows:

$$w(x=0,t)=S(t), \; w'(x=0,t)=0, \; w''(x=a,t)=0, \; w'''(x=a,t)=0, \tag{22}$$

wherein w, w', w" and w'" represent displacement, slope, moment and shear in the Z-axis respectively, and S(t) is the displacement inputted from the fixed end. The four constants $w_{rp}$, $w_{lp}$, $w_{re}$ and $w_{le}$ can be solved by the boundary conditions.

Taking equation (21) into the piezoelectric sensor equation (16) through Fourier transformation, we obtain:

$$q(k) = -z^0 e_{31}^0 k^2 \int_0^a \varsigma(x)(-w_{lp}e^{ikx} + w_{le}e^{kx} - w_{rp}e^{-ikx} + w_{re}e^{-kx})dx, \tag{23}$$

From this integration equation, through the use of structural wave propagating factors ($e^{\pm kx}$, $e^{\pm ikx}$) and distributed integration characteristic of the piezoelectric material, we can obtain by multiplying the effective surface electrode function ξ(x) by a Heaviside step function H(x-a) for Laplace transformation:

$$L[\varsigma(x); p] = \int_0^\infty H(x-a)\varsigma(x)e^{-px}dx, \tag{24}$$

wherein p can be ±k, ±ik. Equation (23) is the main idea of the spatial filter since the frequency spectrum of the charge signal obtained from the piezoelectric sensor can be designed by modulating the effective surface electrode function $\xi(x)$ of the piezoelectric material. The surface electrode function can be a Laplace transform function for selecting a filtering effect and facilitating a connection with a control loop. The Heaviside step function H(x-a) has an effect similar to the window function in the signal processing method. A properly selected window function can reduce the spectrum leakage. Specifically, the window function under the general condition will not influence the result of the effective surface electrode function $\xi(x)$ after Laplace transformation. Harris discussed in detail in 1978 kinds of window functions and constructed the following Table 1.

Compared to the electronic filter, the most outstanding feature of the spatial filter is that kinds of filtering effects can be selected through functions in the Laplace transformation table. Most importantly, we can select the function which has a phase in the polar coordinates independent of the wave number after transformed, in order that only the gain of the filter is modulated without the modulation of its phase. An extreme freedom for designing the control loop for a control system is thus obtained. As an example, if the shape of the effective surface electrode $\omega(x)=\sin(rx)$, the charge signal q(t) measured by the spatial filter will be the addition of the filtered frequency spectrum in the following equation:

TABLE 1

| Window | Highest Side-Lobe Level(dB) | Side-Lobe Fall-off (dB/OCT) | Coherent Gain | Equiv. Noise BW (BINS) | 3.0 dB BW (BINS) | Scallop Loss (dB) | 6.0 dB BW (BINS) |
|---|---|---|---|---|---|---|---|
| Rectangle | −13 | −6 | 1.00 | 1.00 | 0.89 | 3.92 | 1.21 |
| Triangle | −27 | −12 | 0.5 | 1.33 | 1.28 | 1.82 | 1.78 |
| $\cos^\alpha(x)$ | | | | | | | |
| $\alpha = 1.0$ | −23 | −12 | 0.64 | 1.23 | 1.20 | 2.10 | 1.65 |
| $\alpha = 2.0$ | −32 | −18 | 0.50 | 1.50 | 1.44 | 1.42 | 2.00 |
| $\alpha = 3.0$ | −39 | −24 | 0.42 | 1.73 | 1.66 | 1.08 | 2.32 |
| $\alpha = 4.0$ | −47 | −30 | 0.38 | 1.94 | 1.86 | 0.86 | 2.59 |
| Hamming | −43 | −6 | 0.54 | 1.36 | 1.3 | 1.78 | 1.81 |
| Riesz | −21 | −12 | 0.67 | 1.20 | 1.16 | 2.22 | 1.59 |
| Riemann | −26 | −12 | 0.59 | 1.3 | 1.26 | 1.89 | 1.74 |
| Bohman | −46 | −24 | 0.41 | 1.79 | 1.71 | 1.02 | 2.38 |
| Poisson | | | | | | | |
| $\alpha = 2.0$ | −19 | −6 | 0.44 | 1.3 | 1.21 | 2.09 | 1.69 |
| $\alpha = 3.0$ | −24 | −6 | 0.32 | 1.65 | 1.45 | 1.46 | 2.08 |
| $\alpha = 4.0$ | −31 | −6 | 0.25 | 2.08 | 1.75 | 1.03 | 2.58 |
| Hanning-Poisson | | | | | | | |
| $\alpha = 0.5$ | −35 | −18 | 0.43 | 1.61 | 1.54 | 1.26 | 2.14 |
| $\alpha = 1.0$ | −39 | −18 | 0.38 | 1.73 | 1.64 | 1.11 | 2.30 |
| $\alpha = 2.0$ | None | −18 | 0.29 | 2.02 | 1.87 | 0.87 | 2.65 |
| Cauchy | | | | | | | |
| $\alpha = 3.0$ | −31 | −6 | 0.42 | 1.48 | 1.34 | 1.71 | 1.90 |
| $\alpha = 4.0$ | −35 | −6 | 0.33 | 1.75 | 1.50 | 1.36 | 2.20 |
| $\alpha = 5.0$ | −30 | −6 | 0.28 | 2.06 | 1.68 | 1.13 | 2.53 |
| Gaussian | | | | | | | |
| $\alpha = 2.5$ | −42 | −6 | 0.51 | 1.39 | 1.33 | 1.69 | 1.86 |
| $\alpha = 3.0$ | −55 | −6 | 0.43 | 1.64 | 1.55 | 1.25 | 2.18 |
| $\alpha = 3.5$ | −69 | −6 | 0.37 | 1.90 | 1.79 | 0.94 | 2.52 |
| Dolph-Chebyshev | | | | | | | |
| $\alpha = 2.5$ | −50 | 0 | 0.53 | 1.39 | 1.33 | 1.70 | 1.85 |
| $\alpha = 3.0$ | −60 | 0 | 0.48 | 1.51 | 1.44 | 1.44 | 2.01 |
| $\alpha = 3.5$ | −70 | 0 | 0.45 | 1.62 | 1.55 | 1.25 | 2.17 |
| $\alpha = 4.0$ | −80 | 0 | 0.42 | 1.73 | 1.65 | 1.10 | 2.31 |
| Kaiser-Bessel | | | | | | | |
| $\alpha = 2.0$ | −46 | −6 | 0.49 | 1.50 | 1.43 | 1.46 | 1.99 |
| $\alpha = 2.5$ | −57 | −6 | 0.44 | 1.65 | 1.57 | 1.20 | 2.20 |
| $\alpha = 3.0$ | −69 | −6 | 0.40 | 1.80 | 1.71 | 1.02 | 2.39 |
| $\alpha = 3.5$ | −82 | −6 | 0.37 | 1.93 | 1.83 | 0.89 | 2.57 |
| Exact Blackman | −51 | −6 | 0.46 | 1.57 | 1.52 | 1.33 | 2.13 |

Accordingly, all tools, e.g. Laplace transformation table or window function table, for designing the spatial filter has been matured for a long time. Also, the filtering effect of the spatial filter is designed with respect to the wave number k having a relationship with frequency $\omega$ determined by the dispersion relationship as equation (20).

$$L[\sin(rx); \pm k] = \frac{r}{k^2 + r^2} = \frac{r}{\sqrt{\frac{\rho A}{EI}\omega + r^2}}, \quad (25)$$

-continued $$L[\sin(rx); \pm k] = \frac{r}{-k^2 + r^2} = \frac{r}{-\sqrt{\frac{\rho A}{EI}\omega + r^2}}, \quad (26)$$

Figure 7:
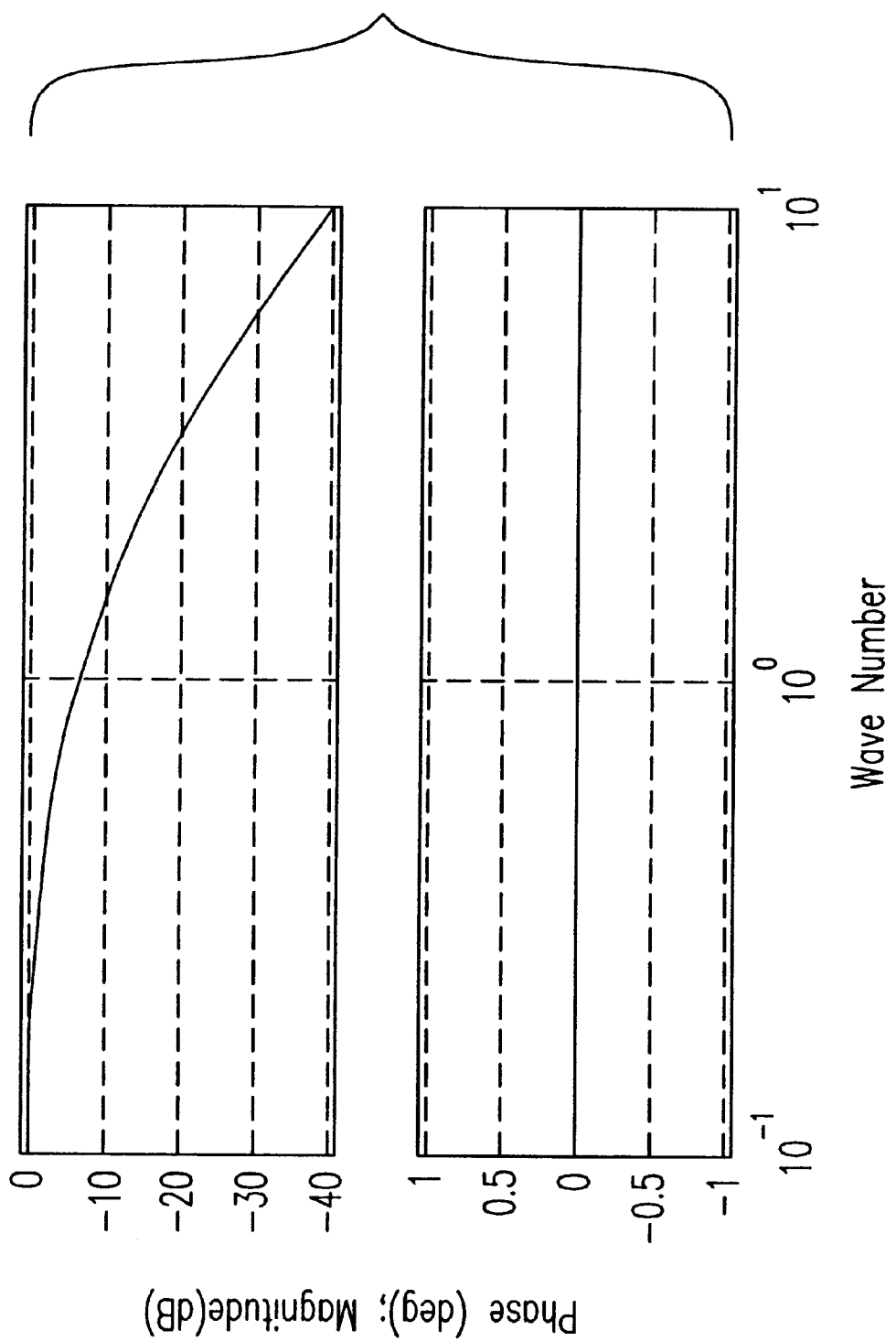
FIG. 7 is a Bode gain phase plot of a spatial filter at the frequency spectrum of $1/(-k2+1)$ for a preferred embodiment of a vibration measuring device according to the present invention.
Figure 8:
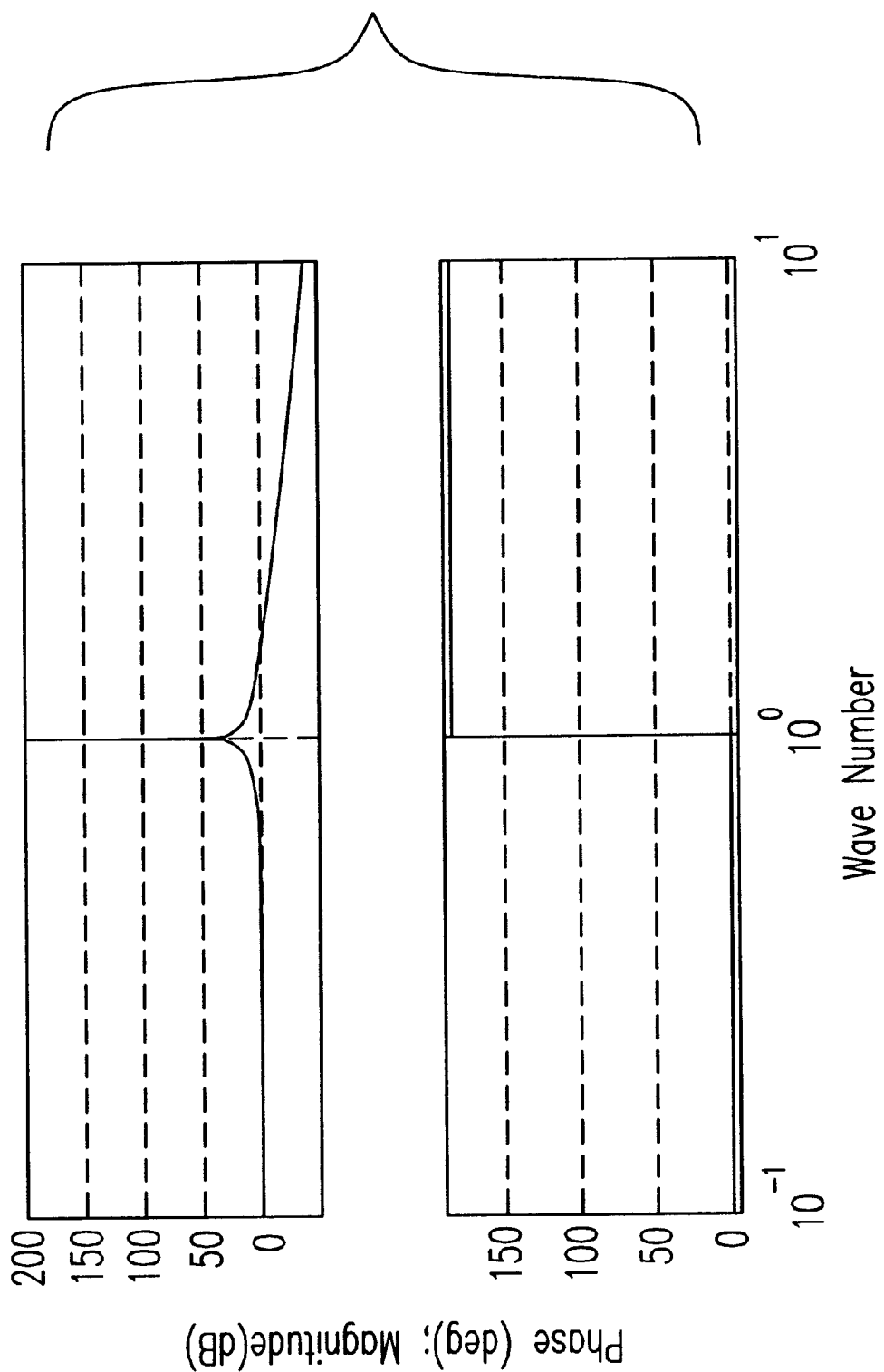
FIG. 8 is a Bode gain phase plot of a spatial filter at the frequency spectrum of $1/(k2+1)$ for a preferred embodiment of a vibration measuring device according to the present invention.

Setting r=1, the Bode plots for the wave number domain are shown in FIGS. 7 and 8. This is a 2-step low-pass filter at r2 in the wave number domain but is a 1-step low-pass filter in the frequency domain. It is to be noticed that the phase in FIG. 7 has no change.

The same method can be used to design spatial filters on other structures, e.g. shaft or bar with the only exception that for each respective structure, the number of the wave propagating factor is the same with that of the step of the structure basic equation. In the general structure, the most step number of the beam is 4 and thus the number of the wave propagating factor ($e^{\pm kx}$, $e^{\pm ikx}$) is 4. If the basic equation of a structure, e.g. a shaft is 2-step, there will be 2 wave propagating factors. It is to be noticed that the fewer the number of the wave propagating factor is, the more the freedom on designing the frequency spectrum of the filtering wave. Taking the structure basic equation for the shaft as an example for illustration:

$$\frac{\partial^2 \theta}{\partial t^2} = \frac{G}{\rho}\frac{\partial^2 \theta}{\partial x^2} \quad (27)$$

wherein θ is the twisted angle, x is the value in the longitudinal axis, G is the shear modulus and σ is the material density. Since this structure basic equation is $2^{nd}$ order, the wave propagating factor ($e^{\pm ikx}$) is two propagating waves. So that designing point distributed sensor with shaft structure will be more free than with beam structure which has two evanescent waves in addition. An example for point distributed sensor design using a shaft for the sensor body can be that as shown in FIG. 9.

4) Modal Sensor

The modal sensor invented in 1980s can be regarded as a special instance of the spatial filter under broad definition. In flexible structure control, the structural vibration is controlled by point sensor and point actuator before the 1980s. Generally some instability issues such as spillover will be encountered upon applying the point sensor. In other words, since the point sensor in the control loop cannot effectively recognize the signal of the uncontrolled vibration mode, the whole system will thus become unstable. (Balas, 1978)

In 1980s, for overcoming the above difficulties, so-called pre-filter and modal filter were continuously discussed and applied to the control system of mutually independent modes. (Meirovitch, 1982) It is to be noticed that the modal filter is referred to the spatial domain and is not used to filter in the time domain as in the conventional filter (Meirovitch, 1985) so that the modal sensor can be considered as a special instance of the spatial filter under broad definition.

To execute the modal analysis for 1-dimension Euler beam, the transverse displacement w can be decomposed to be summation of all modes (Blevins, 1985):

$$w(x, t) = \sum_{m=1}^{\infty} A_m(t)\Phi_m(x), \quad (28)$$

wherein $A_m(t)$ represents the modal coordinate of the $m^{th}$ mode whereas $\Phi_m(x)$ represents the mode shape of the $m^{th}$ mode. Taking equation (28) into equation (17), we can obtain the piezoelectric sensor equation:

$$q(t) = \sum_{m=1}^{\infty} A_m(t)B_m, \quad (29)$$

wherein $$B_m = -z^0 e_{31}^0 \int_0^a \left[\varsigma(x)\frac{d^2\Phi_m(x)}{dx^2}\right]dx. \quad (30)$$

Modes are mutually normal. For a cantilever beam, the modal shape can be expressed as follows: (Blevins, 1985)

$$\Phi_m = \left[\cosh\left(\frac{\lambda_m x}{a}\right) - \cos\left(\frac{\lambda_m x}{a}\right)\right] - \sigma_m\left[\sinh\left(\frac{\lambda_m x}{a}\right) - \sin\left(\frac{\lambda_m x}{a}\right)\right] \quad (31)$$

wherein $\lambda_m$ is the structural eigen value, $\sigma_m$ is the natural frequency parameter and equals to $(\sinh\lambda_m - \sin\lambda_m)/(\cosh\lambda_m + \cos\lambda_m)$, $\lambda_1 = 1.87510407$, $\lambda_2 = 4.69409113$, $\sigma_1 = 0.734095514$ and $\sigma_2 = 1.018467319$. The normal characteristic between modes can be derived as follows:

$$\int_0^a \left[\frac{d^2\Phi_n(x)}{dx^2}\right]\left[\frac{d^2\Phi_m(x)}{dx^2}\right]dx = \delta_{nm}\left[\frac{\lambda_m^4}{a^3}\right], \quad (32)$$

wherein $\delta_{mn}$ is Kronecker delta. If the effective surface electrode function is expressed as:

$$\varsigma(x) = \frac{\mu_n a^3}{\lambda_n^4}\frac{d^2\Phi_n(x)}{dx^2}, \quad (33)$$

wherein $\mu_n$ is the proportion constant in the electrode design and the lower index is the $n^{th}$ mode, we can obtain the following modal sensor equation by taking equations (30) to (33) into equation (29):

$$q(t) = -z^0 e_{31}{}^0\mu_n A_n(t), \quad (34)$$

By differentiating the above equation, we can obtain:

$$i(t) = \frac{dq(t)}{dt} = -z^0 e_{31}^0 \mu_n \frac{dA_n(t)}{dt} \quad (35)$$

From the above equation, it can be known that the piezoelectric modal sensor can directly measure the differentiation of the specific modal coordinate. In other words, the modal sensor will not have an effect of modal spillover.

The modal sensor serving as an active point distributed sensor of a relatively lower sensitivity can in fact be regarded as a structural matching filter and can lift the bandwidth limitation resulting from the sensing structure resonance through the manufacture of the higher modal sensor. Raising the bandwidth to an even higher mode is another new concept according to the present invention. Specifically, in order to eliminate the sensor sensitivity with respect to the mode 1, the most direct method is to manufacture a second modal sensor or a multi-modal sensor for a broader bandwidth.

The next problem to be considered is how much process gain can be obtained by adopting the modal sensor or the multi-modal sensor. The higher the modal number of modal sensor is, although the higher the sensor bandwidth will be in response to the raise of the sensed resonance level, the poorer the low frequency sensitivity will be, which will result in the reduction of the process gain. Accordingly, the optimum design cannot be obtained by sticking to the increased mode number of the modal sensor.

5) Anti-mode 1 Sensor

Figure 10:
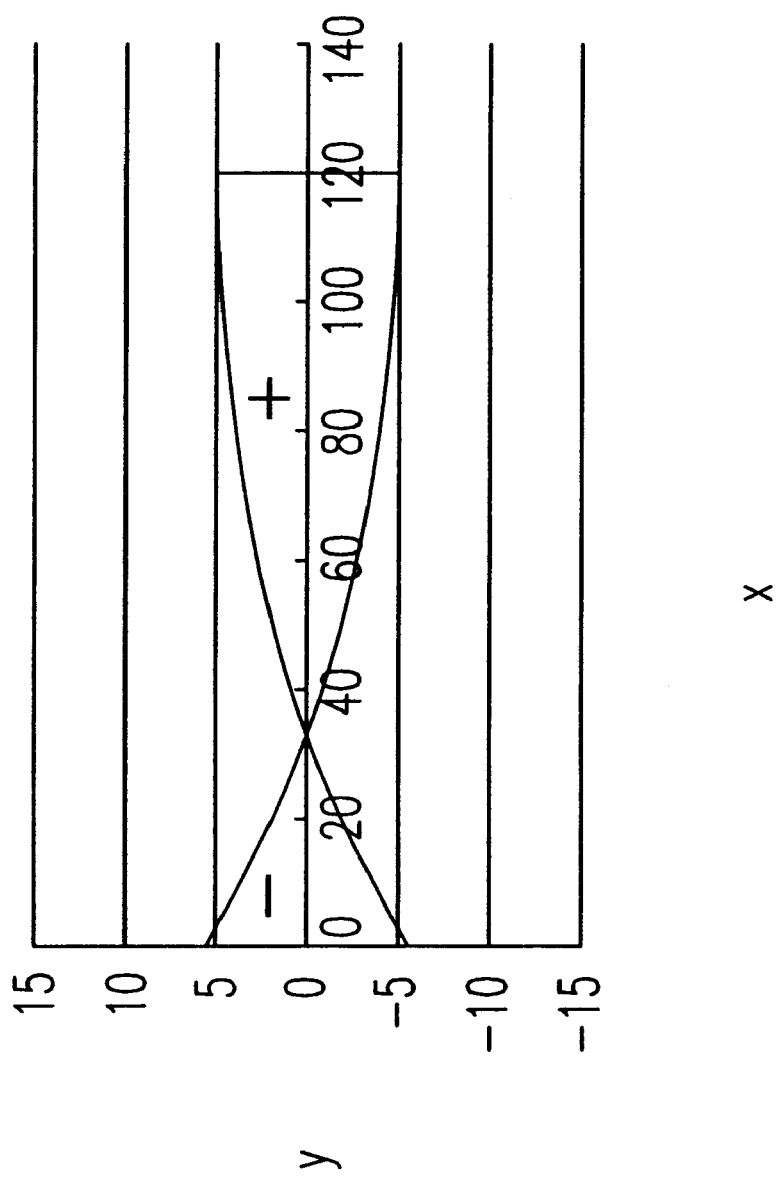
FIG. 10 is a schematical shape plot showing an electrode function of an anti-mode 1 sensor according to a preferred embodiment of a vibration measuring device of the present invention.

Following the preceding section, by adopting the linearity theory, the multi-modal sensor signal equals to the summation of all respective modal sensor signals. The more modes the multimodal sensor is, the better the process gain will be. Therefore, concept of an anti-mode 1 sensor was produced. Applying the assumption and design concept of the modal sensor, the anti-mode sensor can be developed merely by eliminating the mode relevant factor in the effective surface electrode. Thus, we can select the effective surface electrode function to be:

$$\varsigma(x) = [H(x) - H(x-a)] - A_1 \frac{d^2\Phi_1}{dx^2} = \sum_{j=2}^{\infty} A_j \frac{d^2\Phi_j}{dx^2} \tag{36}$$

for eliminating the sensor sensitivity with respect to the mode 1. Through the eigen-function expansion, we can obtain:

$$A_n = \frac{a^2}{\lambda_n^3}[(\sinh(\lambda_n) + \sin(\lambda_n)) - \sigma_n(\cosh(\lambda_n) - \cos(\lambda_n))], \tag{37}$$

wherein n=1~∞. By taking equation (37) into equation (36), the effective surface electrode equation of the anti-mode 1 sensor can be obtained. With the piezoelectric sensing layer being an anti-mode sensor, the present measuring device can serve as an active point distributed sensor of a relatively lower sensitivity. In fact, the effective surface electrode function can be cut into the shape in FIG. 10 wherein the positive and negative signs represent opposite polarities of the surface electrode. Specifically, the anti-mode 1 sensor has a surface electrode having an inverse polarity with respect to the mode 1 sensor, and has a vertically symmetrical shape for increasing a profile of the charge signal. In addition, the anti-mode 1 sensor cancels an error signal resulting from rotation in the X-axis. The signal obtainable by the anti-mode 1 sensor can be expressed as follows:

$$i(t) = z^0 e_{31}^0 \sum_{n=2}^{\infty} \mu_n A_n' \frac{dA_n(t)}{dt}, \tag{38}$$

It can be clearly known from equation (38) that there will be no mode 1 contribution. As the anti-mode 1 sensor has been theoretically proved to be possibly existent, the bandwidth limitation of the piezoelectric accelerometer will shift from the original first resonant frequency to a second resonant frequency so that a flexible structure can be used for the sensing body for reducing a bulk thereof and raising a low frequency response effect thereof 6) Point Distributed Sensor Kinds of advantages discussed hereinbefore are only referred to the distributed piezoelectric sensor in the past. Through above analyses, it can be known that the distributed sensor in use has many advantages very different from those of the conventional point sensor. From the viewpoint of a designer, however, the distributed sensor should be separately designed with respect to different structure body so that it is not so popular as the point sensor. One of main features of the present invention is to provide a point distributed piezoelectric sensor by gathering together advantages of distributed sensor and point sensor. By applying kinds of bandwidth modulation methods using the wave number domain to the point sensor body, the piezoelectric sensor needs only be designed one time with respect to the simple sensor structure, and the completed point sensor still has the effect of bandwidth selection. Such design concept of point distributed sensor will allow the point sensor to bear at the same time the advantages of a distributed sensor.

It is to be noticed that design tools for the spatial filter are Laplace transformation table and window function both of which have been maturely developed. The modulation of the spatial wave number domain by Laplace transformation can be used to achieve the filtering function without the limitation of Bode gain phase theorem, through the selection of the effective surface electrode function type after Laplace transformed. Accordingly, a sensor of spatial filtering function having the modulated gain without the influence on the phase angle can be obtained. With application of the suitable window functions, the filtering effect can be optimized. Such a spatial filter will not result in any unnecessary phase lag but has a freely selective bandwidth, which is an entirely new and highly utility technique for a control system.

Conventionally, the low frequency accelerometer has an extensive application scope, e.g. for measuring the vibration of the building structure, controlling the low frequency feedback of the sound equipment or detecting the movement of troops. Due to the problem of the mechanical impedance, the accelerometer has a large bulk. The larger the bulk is, the more difficult it can be manufactured or carried, the less its first resonant frequency will be, and the fewer the applicable bandwidth will be. Generally, the bandwidth of the accelerometer is from one fifth to one tenth of its first resonant frequency. Accordingly, there have been key issues about how to reduce the bulk of the low frequency accelerometer, how to increase its applicable bandwidth at the same time and how to simplify its manufacturing method. Nowadays, the semiconductor manufacturing procedure has been wonderfully developed so that the semiconductor sensor will have advantages of high precision and low cost. Nevertheless, for a low frequency accelerometer, it cannot be adapted into the semiconductor manufacturing process since the mechanical impedance problem cannot be solved.

In order to overcome the above problem, the simplest way to reduce the accelerometer bulk is to select a flexible structure rather than the conventional block structure, which will entail the issue of decreasing the applicable bandwidth. The accelerometer bandwidth can easily be increased through the introduction of the matching spatial filter and the full utilization of the mutually normal relation between modes, by reconsidering this problem with the design concept of the distributed sensor. Specifically, the accelerometer bandwidth is limited to the first vibration mode in the past. If the sensitivity of the sensing element with respect to the first vibration mode is eliminated, that is to say, an anti-mode 1 sensor has been made, the entire accelerometer transformation functions will not subject to the influence of the first vibration mode of the sensor structure so that the accelerometer bandwidth can relatively be increased. As such for design, not only the low frequency accelerometer bandwidth can be effectively increased, but the accelerometer bulk can be reduced to make its application more convenient.

7) Active Point Distributed (POD) Sensor

As the design concept of an active accelerometer, the point distributed sensor can be accordingly designed. To design the vibration control loop for the sensor structure, there already are design parameters, e.g. PID controller or phase lag or lead compensator in the classical automatical control theory.

Figure 11B:
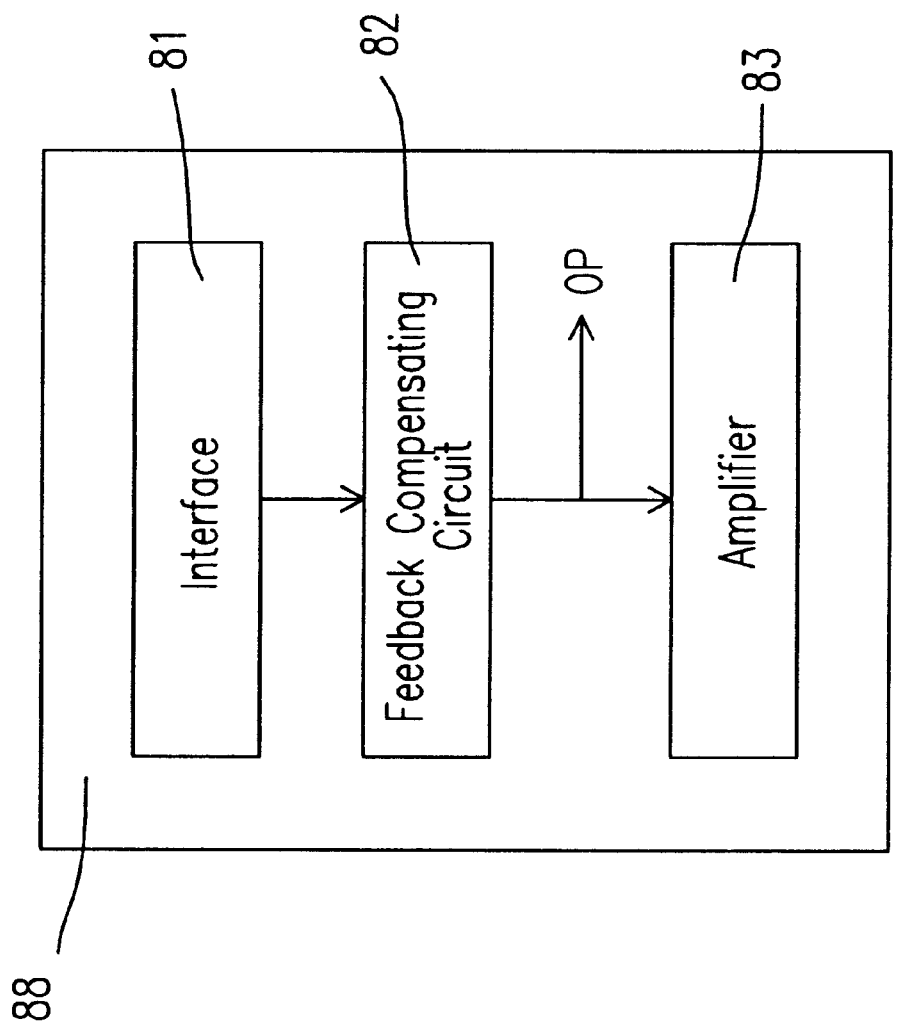

As shown in FIG. 11B, there is schematically shown an entire control loop architecture. The arrowy sign IP indicates the input direction of the acceleration signal. Under such control design, through the introduction of the distributed sensor 80 of selective frequency designed with the sensor structure 61 and the vibration control loop, the signal of selective bandwidth sensed by the point distributed sensor 80 can be feedbacked to the actuator 70 through the interface circuit 81, the feedback compensating circuit 82 and the amplifier 83. Accordingly, the deformation of the sensor structure 61 resulting from the input signal will be reduced. Under such situation, since the structural deformation is nearly zero, the deformation of the sensor structure 61 will have a more linear relation with the signal to be measured. In such architecture, the signal obtainable from the OP point and proportional to the feedback signal provided to the actuator 70 will be the very precise measured signal of the selected bandwidth.

On the other hand, by using a modal sensor to control feedback for the sensor structure, the sensor sensitivity of the entire feedback transfer functions to that specific mode will be reduced. For an accelerometer design, this means that the resonant frequency can be modified by the feedback circuit, so can be the available bandwidth. As in the previous system, the signal proportional to the feedback signal provided to the actuator is the desired measured signal. Such design concept is viable if the modal sensor is changed into an anti-mode sensor.

In sum, through the application of the distributed piezoelectric sensing layer, the originally limited bandwidth can now be designed as required for selectively sensing in different frequency domains to overcome the shortcomings encountered by the conventional point sensor.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

What is claimed is:

1. A vibration measuring device for measuring a vibration of an object comprising:
    a sensing body generating a dynamic information in response to said vibration;
    a piezoelectric sensing layer disposed on said sensing body to construct thereby a sensor and formed in a distributed mode to measure said dynamic information in a selected specific bandwidth;
    an actuator connected to said sensing body; and
    a feedback circuit electrically connected to said piezoelectric sensing layer and said actuator for receiving a measured signal produced by said piezoelectric sensing layer and transmitting a feedback signal to said actuator for controlling a deformation of said sensing body, wherein said feedback circuit includes a proportion/integration/differentiation (PID) controller, and one of a phase lag compensator and a phase lead compensator.

2. A vibration measuring device according to claim 1 wherein:
    said sensor is a point sensor;
    said object is one selected from a group consisting of building structure, sound equipment and military mechanics;
    said sensing body is a sensor structure body; and
    said piezoelectric layer has an effective piezoelectric profile.

3. A vibration measuring device according to claim 2 wherein said device is one selected from a group consisting of an accelerometer, a device for metering acceleration rate and a force sensor.

4. A vibration measuring device according to claim 3 wherein said accelerometer, said metering device and said force sensor respectively have sensor structure bodies respectively having different dynamic informations.

5. A vibration measuring device according to claim 2 wherein:
    said sensing layer includes two piezoelectric sheets adhered with each other and respectively having two piezoelectric surfaces for sensing in said specific bandwidth; and
    said two piezoelectric surfaces respectively adhere thereto two surface electrodes collectively forming an effective surface electrode for generating said effective piezoelectric profile.

6. A vibration measuring device according to claim 5 wherein said two piezoelectric sheets are oppositely polarized in said effective surface electrode and have an electromagnetic interference shielding effect through a pseudo ground.

7. A vibration measuring device according to claim 5 wherein said sensing layer has polarized profile and direction through a potential difference.

8. A vibration measuring device according to claim 7 wherein said potential difference of said sensing layer results in a sensing charge along a thickness of said sensing layer, and said sensing charge being a charge signal in said effective surface electrode is to be generated by said effective surface electrode.

9. A vibration measuring device according to claim 8 wherein said effective surface electrode has a specific shape determined by a surface electrode function for determining said specific shape in response to respective said sensing body.

10. A vibration measuring device according to claim 9 wherein said surface electrode function is a weighting function, and said charge signal is presented by a frequency spectrum and modulated by said weighting function.

11. A vibration measuring device according to claim 10 wherein said surface electrode function cooperates with a Heaviside step function for reducing a leaking phenomenon of said frequency spectrum.

12. A vibration measuring device according to claim 10 wherein:
    said measuring device is a sensor system;
    said vibration of said object results in a number of space waves in a sensing space; and
    an integration of said surface electrode function in said sensing space can overcome a phase delay phenomenon of said space waves resulting from a modulated gain of said sensor system.

13. A vibration measuring device according to claim 12 wherein a phase angle of said space waves is kept constant for simultaneously obtaining past, present and future information of said space waves in order that said measuring device serves as a spatial filter of broad bandwidth or selective bandwidth.

14. A vibration measuring device according to claim 13 wherein said surface electrode function is a Laplace transform function for selecting a filtering effect and facilitating a connection with a control loop.

15. A vibration measuring device according to claim 9 wherein said piezoelectric sensing layer is a mode 1 sensor being a matching filter of said sensing body.

16. A vibration measuring device according to claim 15, further comprising a second modal sensor for a broader bandwidth.

17. A vibration measuring device according to claim 16 wherein said second modal sensor is determined by a second surface electrode function for eliminating a sensitivity with respect to said mode 1 sensor and said second surface electrode function is obtained through expansion from an eigen function so that said second modal sensor is an anti-mode 1 sensor.

18. A vibration measuring device according to claim 17 wherein said anti-mode 1 sensor has a surface electrode having an inverse polarity with respect to said mode 1 sensor, and has a vertically symmetrical shape for increasing a profile of said charge signal.

19. A vibration measuring device according to claim 18 wherein said anti-mode 1 sensor cancels an error signal resulting from rotation in order that said measuring device has a second resonant frequency, and said sensing body is a flexible structure for reducing a bulk thereof and raising a low frequency response effect thereof.

20. A vibration measuring device according to claim 19 wherein:
  said anti-mode 1 sensor is manufactured by a semiconductor procedure; and
  said measuring device is a point distributed sensor serving as a low frequency accelerometer.

21. A vibration measuring device according to claim 1 wherein an effective piezoelectric profile of said piezoelectric sensing layer varies with a thickness modulation of said piezoelectric sensing layer made of one selected from a group consisting of piezoelectric polymer of polyvinylidene fluoride (PVDF), lead zirconate titanate (PZT) and zinc oxide (ZnO).

22. A vibration measuring device according to claim 1 wherein said selected specific bandwidth is a frequency domain selected from a group consisting of low-pass, high-pass, band-pass and band-stop.

23. A vibration measuring device according to claim 1, further comprising a second piezoelectric sensing layer for measuring said dynamic information in a second selected bandwidth.

24. A vibration measuring device according to claim 1 wherein:
  said measuring device is an accelerometer;
  said piezoelectric sensing layer senses said dynamic information to generate one of an electric charge and a voltage signal and is electrically connected to an interface circuit; and
  said interface circuit is provided with an amplifier for amplifying one of said electric charge and said voltage signal to obtain an acceleration signal.

25. A vibration measuring device according to claim 1 wherein:
  said measuring device is a device for metering an acceleration rate;
  said piezoelectric sensing layer senses said dynamic information to generate a current signal and is electrically connected to an interface circuit; and
  said interface circuit is provided with an amplifier for amplifying said current signal to obtain an acceleration rate signal.

26. A vibration measuring device according to claim 1 wherein said sensing body is one of a beam and a shaft.

27. A vibration measuring device according to claim 1 wherein:
  said measuring device is an active point distributed sensor; and
  said feedback circuit includes an interface circuit, a feedback compensation circuit and an amplifier, in which said feedback compensation circuit outputs said measured signal proportional to said feedback signal.

28. A vibration measuring device according to claim 1 wherein said piezoelectric sensing layer is a mode sensor in order that said measuring device serves as an active point distributed sensor of a relatively lower sensitivity.

29. A vibration measuring device according to claim 1 wherein said piezoelectric sensing layer is an anti-mode sensor in order that said measuring device serves as an active point distributed sensor of a relatively lower sensitivity.

30. A vibration measuring device according to claim 1 wherein said measuring device is one selected from a group consisting of an accelerometer, a device for metering acceleration rate and a force sensor.

31. A vibration measuring device according to claim 1 wherein said actuator is a film actuator made of one of polyvinylidene fluoride (PVDF) and lead zirconate titanate (PZT).

32. A vibration measuring device according to claim 1 wherein said actuator is a point actuator made of one of polyvinylidene fluoride (PVDF) and lead zirconate titanate (PZT).

33. A vibration measuring device according to claim 1 wherein said actuator is a distributed actuator driven by one selected from a group consisting of an electric field, a magnetic field and an electromagnetic field.

34. A vibration measuring device according to claim 1 wherein said actuator is a point actuator driven by one selected from a group consisting of an electric field, a magnetic field and an electromagnetic field.

35. A vibration measuring method for measuring a vibration of an object comprising steps of:
  providing a sensing body generating a dynamic information in response to said vibration;
  providing a piezoelectric sensing layer formed in a distributed mode to measure said dynamic information in a selected specific bandwidth;
  providing an actuator; and
  providing a feedback circuit for receiving a measured signal produced by said piezoelectric sensing layer and transmitting a feedback signal to said actuator for controlling a deformation of said sensing body, wherein said feedback circuit includes a proportion/integration/differentiation (PID) controller, and one of a phase lag compensator and a phase lead compensator.

* * * * *